US009655877B2

(12) United States Patent
Lau et al.

(10) Patent No.: US 9,655,877 B2
(45) Date of Patent: May 23, 2017

(54) THERAPEUTIC METHODS FOR TREATING INFLAMMATION AND IMMUNE SYSTEM DISORDERS

(75) Inventors: Allan Sik Yin Lau, Hong Kong (CN); Lai Hung Cindy Yang, Hong Kong (CN); Cho Tsun Or, Hong Kong (CN)

(73) Assignees: VERSITECH LIMITED, Hong Kong (CN); BAGI RESEARCH LIMITED, Hong Kong (CN)

( * ) Notice: Subject to any disclaimer, the term of this patent is extended or adjusted under 35 U.S.C. 154(b) by 269 days.

(21) Appl. No.: 13/005,301

(22) Filed: Jan. 12, 2011

(65) Prior Publication Data

US 2011/0177106 A1  Jul. 21, 2011

Related U.S. Application Data

(63) Continuation-in-part of application No. PCT/IB2010/003050, filed on Nov. 8, 2010.

(60) Provisional application No. 61/263,517, filed on Nov. 23, 2009.

(51) Int. Cl.
*A61K 31/343* (2006.01)

(52) U.S. Cl.
CPC .................................. *A61K 31/343* (2013.01)

(58) Field of Classification Search
CPC .. A61K 31/343; A61K 31/365; C07D 307/88; A61P 29/00
See application file for complete search history.

(56) References Cited

U.S. PATENT DOCUMENTS

| 2003/0165580 | A1 | 9/2003 | Zhao | |
| 2010/0298427 | A1* | 11/2010 | Fowler et al. | 514/470 |

FOREIGN PATENT DOCUMENTS

| CN | 1810241 | 8/2006 |
| CN | 1977839 A | 6/2007 |
| CN | 101184484 A | 5/2008 |
| JP | A 2008-542226 A | 11/2008 |
| WO | WO 95/00157 | 1/1995 |
| WO | WO 2006/125651 | 11/2006 |
| WO | WO 2008/006581 | 1/2008 |
| WO | WO 2008/017491 A1 | 2/2008 |

OTHER PUBLICATIONS

Yan et al. "Pharmacokinetics and Metabolism of Ligustilide, a Majore Bioactive Component in Rhizoma Chuanxiong, in the Rat" Drug Metabolism and Disposition, 2008, vol. 36, No. 2, pp. 400-408.*
Son et al. "Inhibitors of Nitric Oxide Synthesis and TNF-alpha Expression from Magnolia obovata in Activated Macrophages" Planta medica, 2000, vol. 66, pp. 469-471.*
Liu et al. "Phthalide Lactones from Ligusticum chuanxiong Ingivit Lipopolysaccharide-Induced TNF-alpha Production and TNF-alpha-Mediated NF-kappa beta Activation" Planta Medica, 2005, vol. 71, pp. 808-813.*
Ling et al. "DL-3-n-butylphthalide protects endothelial cells agaist oxidative/nitrosative stress, mitochondrial damage and susequent cell death after oxygen glucose deprivation in vitro" Brain Research, Jul. 2009, vol. 1290, pp. 91-101.*
Lenon et al. "Inhibition of inducible nitric oxide production and iNOS protein expression in lipopolysaccharide-stimulated rat aorta and Raw 264.7 macrophages by ehanol extract of a Chinese herbal medicine formula (RCM-101 for allergic rhinitis" Journal of Ethnopharmacology, 2008, vol. 116, pp. 547-553.*
Kuang et al. "Protective effect of Z-lingustilide against amyloid beta-induced neurotoxicity is associated with decrease pro-inflammatory markers in rat brains" Pharmacology, Biochemistry and Behavior, Mar. 2009, pp. 635-641.*
Andreasen et al. "Human Endotoxemia as a Model of Systemic Inflammation" Current medicinal Chemistry, 2008, vol. 15, pp. 1697-1705.*
Sheridan "The Most Common Chemical Replacements in Drug-Like Compounds" J. Chem. Inf. Comput. Sci., 2002, vol. 42, pp. 103-108.*
J. G. Cannon Chapter Nineteen in Burger's Medicinal Chemistry and Drug Discovery, Fifth Edition, vol. I: Principles and Practice, Wiley-Interscience 1995, pp. 783-802, 784.*
Sheridan "The Most Common Chemical Replacements in Drug-Like Compounds" J. Chem. Inf. Comput. Sci., 2002, 42, 103-108.*
Zheng et al. "The antipsychotic siperone attenuates inflammatory response in cultured microglia via the reduction of proinflammatory cytokine expression and nitric oxide production", Journal of Neurochemistry, 2008, vol. 107, pp. 1225-1235.*
Kim et al. "Histon Deacetylase Inhibitors Exhibit Anti-Inflammatory and Neuroprotective Effects in a Rat Permanent Ischemic Model of Stroke: Multiple Mechanisms of Action" The Journal of Pharmacology and Experimental Therapeutics, 2007, vol. 321, pp. 892-901.*
Liu et al. "Tumor Necrosis Factor-alpha Expression in Ischemic Neurons", Stroke, 1994, vol. 25, pp. 1481-1488).*
Aggarwal et al. "Inflammation and cancer: how hot is the link?" *Biochem Pharmacol.*, 2006, pp. 1605-1621, vol. 72.
Barone et al. "Inflammatory mediators and stroke: New opportunities for novel therapeutics." *Journal of Cerebral Blood Flow and Metabolism*, 1999, pp. 819-834, vol. 19.
Blasi et al. "Immortalization of Murine Microglial Cells by a V-Raf/V-Myc Carrying Retrovirus" *Journal of Neuroimmunology*, 1990, pp. 229-237, vol. 27.

(Continued)

*Primary Examiner* — Kendra D Carter
(74) *Attorney, Agent, or Firm* — Saliwanchik, Lloyd & Eisenschenk

(57) ABSTRACT

The subject invention provides novel and advantageous materials and methods for treating neuroinflammation, neurodegenerative disease, and cerebrovascular disease by modulating TNF-α and/or nitric oxide production. Specifically exemplified herein is the therapeutic use of senkyunolide A (Sen A) and Z-ligustilide (Z-Lig), compounds isolated from traditional Chinese medicinal material *Ligusticum chuanxiong* (LCX).

2 Claims, 10 Drawing Sheets

(56) References Cited

OTHER PUBLICATIONS

Bone R.C. "Gram-negative sepsis. Background, clinical features, and intervention" *Chest*, 1991, pp. 802-808, vol. 100.

Chamorro et al. "The harms and benefits of inflammatory and immune responses in vascular disease" *Stroke*, 2006, pp. 291-293, vol. 37.

Cheng et al. "HIV-1 transactivator protein induction of suppressor of cytokine signaling-2 contributes to dysregulation of IFN{gamma} signaling" *Blood*, 2009, pp. 5192-5201, vol. 113, No. 21.

Cheng et al. "Interferon-gamma regulation of TNF alpha induced matrix metalloproteinase 3 expression and migration of human glioma T98G cells" *Int J Cancer*, Sep. 15, 2007, pp. 1190-1196, vol. 121, No. 6.

Cheung et al. "A role for double-stranded RNA activated protein kinase PKR in Mycobacterium-induced cytokine expression" *J Immunol.*, Dec. 1, 2005, pp. 7218-7225, vol. 175, No. 11.

Irving et al. "Role of mitogen- and stress activated kinases in ischemic injury" *Journal of Cerebral Blood Flow and Metabolism*, 2002, pp. 631-647, vol. 22.

Kim et al. "Inhibition of p38 and ERK MAP kinases blocks endotoxin induced nitric oxide production and differentially modulates cytokine expression" *Pharmacol Res.*, 2004, pp. 433-439, vol. 49.

Law et al. "Role for nonstructural protein 1 of severe acute respiratory syndrome coronavirus in chennokine dysregulation" *J Virol*, Jan. 2007; Epub Oct. 11, 2006, pp. 416-422, vol. 81, No. 1.

Lee et al. "p38 mitogen activated protein kinase dependent hyperinduction of tumor necrosis factor alpha expression in response to avian influenza virus H5N1" *Journal of Virology*, 2005, pp. 10147-10154, vol. 79.

Li et al. "Mechanisms for HIV Tat upregulation of IL-10 and other cytokine expression: kinase signaling and PKR-mediated immune response" *FEBS Lett.*, Jun. 6, 2005, pp. 3055-3062, vol. 579 No. 14.

Lu et al. "LPS/TLR4 signal transduction pathway" *Cytokine*, 2008, pp. 145-151, vol. 42.

Montesano et al. "Tumour necrosis factor alpha confers an invasive, transformed phenotype on mammary epithelial cells" *J Cell Sci.*, 2005, pp. 3487-3500, vol. 118.

Ohlsson et at "Interleukin-1 receptor antagonist reduces mortality from endotoxin shock" *Nature*, 1990, pp. 550-552, vol. 348.

Raetz, C.R. "Biochemistry of endotoxins" *Annu Rev Biochem.*, 1990, pp. 129-170, vol. 59.

Raetz et al. "Gram-negative endotoxin: an extraordinary lipid with profound effects on eukaryotic signal transduction" *Faseb J.*, 1991, pp. 2652-2660; vol. 5.

Samson et al. "Inflammation and ischaemic stroke: current status and future perspectives" *Revue Neurologique*, 2005, pp. 1177-1182, vol. 161, abstract.

Schmitz et al. "Are circulating monocytes as microglia orthologues appropriate biomarker targets for neuronal diseases?" *Central Nervous Systems Agents in Medicinal Chemistry*, 2009, pp. 307-330, vol. 9.

Shohami et al. "Dual role of tumor necrosis factor alpha in brain injury" *Cytokine & Growth Factor Reviews*, 1999, pp. 119-130, vol. 10.

Tracey et al. "Anti-cachectin/TNF monoclonal antibodies prevent septic shock during lethal bacteraemia" *Nature*, 1987, pp. 662-664, vol. 330.

Tracey et al. "Tumor necrosis factor a pleiotropic cytokine and therapeutic target" *Annu Rev Med.*, 1994, pp. 491-503, vol. 45.

Wang et al. "The inflammatory response in stroke" *Journal of Neuroimmunology*, 2007, pp. 53-68, vol. 184.

Woodworth et al. "Interleukin 1 alpha and tumor necrosis factor alpha stimulate autocrine amphiregulin expression and proliferation of human papillomavirus-immortalized and carcinoma-derived cervical epithelial cells" *Proc Nati Aced Sci U S A*, 1995, pp. 2840-2844, vol. 92.

Yang et al. "Identification of the Bioactive Constituent and Its Mechanisms of Action in Mediating the Anti-inflammatory Effects of Black Cohosh and Related Cimicifuga species on Human Primary Blood Macrophages" *Journal of Medicinal Chemistry*, 2009, pp. 6707-6715, vol. 52.

Yim et al, "HIV-1 Tat dysregulation of lipopolysaccharide induced cytokine responses: microbial interactions in HIV infection" *AIDS*, Jul. 31, 2009, pp. 1473-1484, vol. 23, No. 12.

Beck, John J. et al., "The Structural Diversity of Phthalides from the Apiaceae," *J. Nat. Prod.*, 2007, 70:891-900.

Harada, M. et al., "Antiarteriosclerosis agent which contains butylidene phtalide, Senkyunolide or ligstyride as active component, is claimed," Derwent Abstract Accession No. 1989-282536, Aug. 1989, XP-002402179.

\* cited by examiner

Method 1: Macerate in 95% ethanol at room temperature with continous sonication for 30 min
Method 2: Reflux in 70% ethanol for 30 min
Method 3: Boil in water for 30 min
Method 4: Macerate in water at room temperature with continuous sonication for 30 min
*: With anti-inflammatory effects

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: TNF-a upstream primer

<400> SEQUENCE: 1
ggctccaggc ggtgcttgtc c                                      21

<210> SEQ ID NO 2
<211> LENGTH: 20
<212> TYPE: DNA
<213> ORGANISM: Artificial Sequence
<220> FEATURE:
<223> OTHER INFORMATION: TNF-a downstream primer

<400> SEQUENCE: 2
```

```
agacggcgat gcggctgatg                                           20

<210> SEQ ID NO 3
<211> LENGTH: 20
<212> TYPE: DNA
<213> ORGANISM: Artificial Sequence
<220> FEATURE:
<223> OTHER INFORMATION: GAPDH upstream primer

<400> SEQUENCE: 3
accacagtcc atgccatcac                                           20

<210> SEQ ID NO 4
<211> LENGTH: 20
<212> TYPE: DNA
<213> ORGANISM: Artificial Sequence
<220> FEATURE:
<223> OTHER INFORMATION: GAPDH downstream primer

<400> SEQUENCE: 4
tccaccaccc tgttgctgta                                           20
```

THERAPEUTIC METHODS FOR TREATING INFLAMMATION AND IMMUNE SYSTEM DISORDERS

CROSS-REFERENCE TO RELATED APPLICATION(S)

The present application is a continuation-in-part application of International Application No. PCT/IB2010/003050, filed Nov. 8, 2010, which claims priority to U.S. provisional application Ser. No. 61/263,517 filed Nov. 23, 2009, both which are hereby incorporated by reference herein in their entirety.

BACKGROUND OF THE INVENTION

In response to injury, cancer, microbial invasion, and the like, humans and other animals mount inflammatory responses to control the pathological condition and to initiate a repair process. During inflammation, various immune cells including T-lymphocytes, neutrophils and macrophages are recruited to the site where they produce cytokines to facilitate the immune response. Among these cytokines, tumor necrosis factor-α (TNF-α) is one of the major proinflammatory proteins that mediates the immune response. Although the effects of proinflammatory cytokines are protective, their overproduction may have adverse effects to the host. In fact, uncontrolled induction of proinflammatory cytokines can lead to complications such as hypotension, organ failure and even death[1,2].

During an acute phase of infection such as in the case of sepsis, uncontrolled production of TNF-α is well known to cause deleterious effects to the host. Sepsis is the second most common cause of death in non-coronary intensive care units and the tenth leading cause of death overall in high-income countries[3]. The clinical outcome of infection leading to sepsis is primarily associated with the excessive stimulation of the host immune cells, particularly monocytes or macrophages, by bacterial endotoxins (e.g., lipopolysaccharide [LPS])[4, 5, 6]. Macrophages overstimulated by LPS also produce high levels of mediators such as interleukin-1 (IL-1), IL-6, and TNF-α[7]. These mediators are implicated in the pathogenesis of sepsis and found to be contributing factors to the demise of the host.

In addition to its role in acute phase response, TNF-α has been shown to be involved in the progression of various chronic diseases including tumorigenesis and rheumatoid arthritis (RA). The dysregulation of TNF-α production has been demonstrated to be involved in different stages of tumorigenesis including initiation of tumor growth[8], cell proliferation[9] and invasion[10]. For tumor cell proliferation, TNF-α upregulates specific growth factors to mediate the malignant growth. The cytokine promotes angiogenesis that supports tumor migration, and thus plays a key role in tumor metastasis. For example, glioblastoma migration and induction of matrix metalloproteinases (MMP) are significantly enhanced in response to TNF-α effects[11]. This induction of MMP in glioblastoma T98G cells can be reversed by treatment of the cells with interferon-g[12].

The uncontrolled production of TNF-α is associated with many acute and chronic neurodegenerative conditions, including stroke, brain trauma, spinal cord injury, amyotrophic lateral sclerosis (ALS), Huntington's disease, Alzheimer's disease, and Parkinson's disease. Studies show that TNF-α rapidly upregulates in the brain after injury, and it plays a pivotal role in inflammatory processes. For instance, studies show that cerebrovascular diseases including ischemic stroke are associated with inflammation mediated responses in the neural cells. Also, the enhanced expression of TNF-α has been found in association with glial cells in the substantia nigra of patients with Parkinson's disease.

The toxic effects of TNF-α and its role as a mediator of focal ischemia may involve many other mechanisms in addition to inflammation. For example, increased TNF-α in the brain and blood in response to lipopolysaccharide (LPS) appears to contribute to increased brain stem thrombosis and hemorrhage, and increased stroke sensitivity/risk. Additionally, TNF-α increases blood-brain barrier permeability and produces pial artery constriction, which can contribute to focal ischemic brain injury. Further, there appears to be a direct toxic effect of TNF-α on capillaries. Specifically, TNF-α increases capillary permeability and opens the blood-brain barrier, apparently by increasing matrix-damaging metalloproteinase (gelatinase B) production, which is also expressed early after focal stroke. TNF-α also causes damage to myelin and oligodendrocytes and increases astrocytic proliferation, thus potentially contributing to demyelination and reactive gliosis during brain injury.

Further examples of acute and chronic disease pathogenesis mediated by TNF-α include rheumatoid arthritis and inflammatory bowel diseases. Patients with rheumatoid arthritis have a low grade insidious inflammation in the synovial tissues. It is known that overproduction of TNF-α at the inflamed joint leads to slow destruction of the joint cartilage and surrounding bone.

Additionally, inflammatory responses including TNF-α production may play an important role in the pathogenesis of cerebrovascular diseases including ischemic stroke and cardiovascular diseases (CVD). It has been suggested that TNF-α may destabilize atherogenesis and atherosclerotic plaques leading to their rupture, resulting in myocardial infarction or stroke in CVD patients.

Furthermore, studies have shown that disease pathogenesis mediated by TNF-α can be associated with microbial, bacterial and viral infections. Cytokines such as TNF-α play a role in defending against the invading pathogens such as, for example, mycobacteria, influenza viruses, SARS-coronavirus and retroviruses including HIV. However, many microbes and viruses have also developed various immunosuppressive mechanisms that cause dysfunction of protein signaling kinases and transcription factors as well as other components involved in the TNF-α signaling pathway[13, 14, 15, 16, 17, 18].

In addition to uncontrolled production of TNF-α, immune cells in a diseased condition are activated by cytokines, microbial compounds or both to generate nitric oxide (NO). Generation of nitric oxide is a feature of genuine immune-system cells such as dendritic cells, NK cells, mast cells and phagocytic cells including monocytes, macrophages, microglia, Kupffer cells, eosinophils, and neutrophils as well as other cells involved in immune reactions. Many targets of NO are themselves regulatory molecules, for example transcription factors and components of various signaling cascade.

Additional keys mediators involved in immune response further include interferons such as Interferon-gamma (IFN-γ); the interleukin family such as Interleukin-1 (IL-1), Interleukin-2 (IL-2), Interleukin-3 (IL-3), Interleukin-4 (IL-4), Interleukin-5 (IL-5), Interleukin-6 (IL-6), Interleukin-7 (IL-7), Interleukin-8 (IL-8), Interleukin-9 (IL-9), Interleukin-10 (IL-10), Interleukin-11 (IL-11), Interleukin-12 (IL-12), Interleukin-13 (IL-13), Interleukin-14 (IL-14), Interleukin-15 (IL-15), Interleukin-16 (IL-16), Interleukin-17 (IL-17), Interleukin-18 (IL-18), Interleukin-19 (IL-19), Interleukin-20 (IL-20), Interleukin-21 (IL-21), Interleukin-22 (IL-22), Interleukin-23 (IL-23), Interleukin-24 (IL-24), Interleukin-25 (IL-25), Interleukin-26 (IL-26), Interleukin-27 (IL-27), Interleukin-28 (IL-28), Interleukin-29 (IL-29), Interleukin-30 (IL-30), Interleukin-31 (IL-31), Interleukin-32 (IL-32), Interleukin-33 (IL-33), Interleukin-34 (IL-34), Interleukin-35 (IL-35); the interleukin receptor family; the macrophage inflammatory protein family such as macrophage inflammatory protein 2 (MIP-2) and macrophage inflammatory protein 1α (MIP-1α); macrophage colony-stimulating factor (M-CSF); and monocyte chemotactic protein-1 (MCP-1).

Targeting the uncontrolled production of inflammatory mediators such as TNF-α and nitric oxide has played an increasing role in treating inflammatory and immune conditions. Use of exogenous anti-inflammatory therapeutics would be particularly desirable to control the adverse effects of immune over-activation. In recent years, immunotherapeutics have been developed that aim at the neutralization of TNF-α and suppression of its undesirable proinflammatory effects. For example, as TNF-α exacerbates focal ischemic injury in neurodegenerative diseases, agents for blocking endogenous TNF-α have been shown to be neuroprotective. These agents include soluble TNF-α receptor (Enbrel) and anti-TNF-α antibody (Infliximab). Despite their novelty and efficacy in the arrest of disease progression, they are very expensive therapeutic regimens.

In addition, non-steroid anti-inflammatory drugs (NSAIDs) including aspirin, ibuprofen, and indomethacin are well-known in ameliorating acute and chronic pain associated with inflammatory diseases such as rheumatoid arthritis and inflammatory bowel disease. However, they are not effective in the treatment of advanced stages of rheumatoid arthritis and related autoimmune diseases. For those conditions, steroids and cytotoxic drugs such as methotrexate and cyclophosphamide are used. These drugs are associated with severe adverse effects including gastrointestinal irritation, severe bleeding, and bone marrow suppression.

Stroke is the leading cause of adult disability and the third most prevalent cause of mortality worldwide. There is increasing evidence that inflammation accounts for the progression of ischemic stroke by causing neuronal damages[19,20, 21]. Microglia cells, the resident macrophages in the brain, are activated during ischemia. In response to the compromised state of oxygen supply, the cells generate various inflammatory mediators including TNF-α, nitric oxide, IL-6 and IL-1[22]. Thus, the development of novel therapies directed towards the inhibition of pathological production of TNF-α and NO is needed to aid in the treatment of these acute and chronic immune diseases.

BRIEF SUMMARY OF THE INVENTION

The present invention provides novel and advantageous therapeutic methods for treating inflammation and/or modulating immune responses. In one embodiment, the present invention provides therapeutic methods for treating neuroinflammation.

Specifically exemplified herein is the therapeutic use of senkyunolide A (Sen A) and Z-ligustilide (Z-Lig), compounds isolated from traditional Chinese medicinal material *Ligusticum chuanxiong* (LCX). The therapeutic methods of the subject invention can be used to modulate TNF-α production by administering, to a subject in need of such treatment, an effective amount of an isolated compound having the following formula:

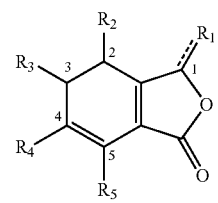

wherein
- - - - - represents a carbon-carbon single bond or a carbon-carbon double bond;

$R_1$ is alkyl or $CR_6$, wherein $R_6$ is alkyl, acyl, haloalkyl, alkylamino or hydroxylalkyl;

$R_2$, $R_3$ and $R_4$ are, independently, —H, acyl, halo, haloalkyl, amino, alkylamino, hydroxyl, alkyl, hydroxylalkyl, or —COOH; and $R_5$ is —H, acyl, halo, haloalkyl, amino, alkylamino, alkyl, hydroxylalkyl, or —COOH.

The subject invention further provides pharmaceutical compositions containing these compounds.

Advantageously, the methods of the present invention can be used to control over-production of TNF-α and nitric oxide in cells associated with inflammation and immune conditions. In addition, the methods of the present invention inhibit cell death induced by cell injury associated with inflammation and immune conditions.

The methods of the present invention are useful for treating conditions selected from, for example, ischemic stroke, autoimmune conditions, rheumatoid arthritis, psoriasis, cardiovascular disease, cerebrovascular disease, neurodegenerative disease, post-infection associated neurological neuralgia or neurasthenia conditions including shingles and chronic fatigue syndrome, inflammatory bowel disorder, septic shock, infections, environmental toxins, intestinal inflammation, allergy, graft rejection, pathological immune cell proliferation or activity, and respiratory inflammation.

BRIEF DESCRIPTION OF THE SEQUENCES

Figure 1:
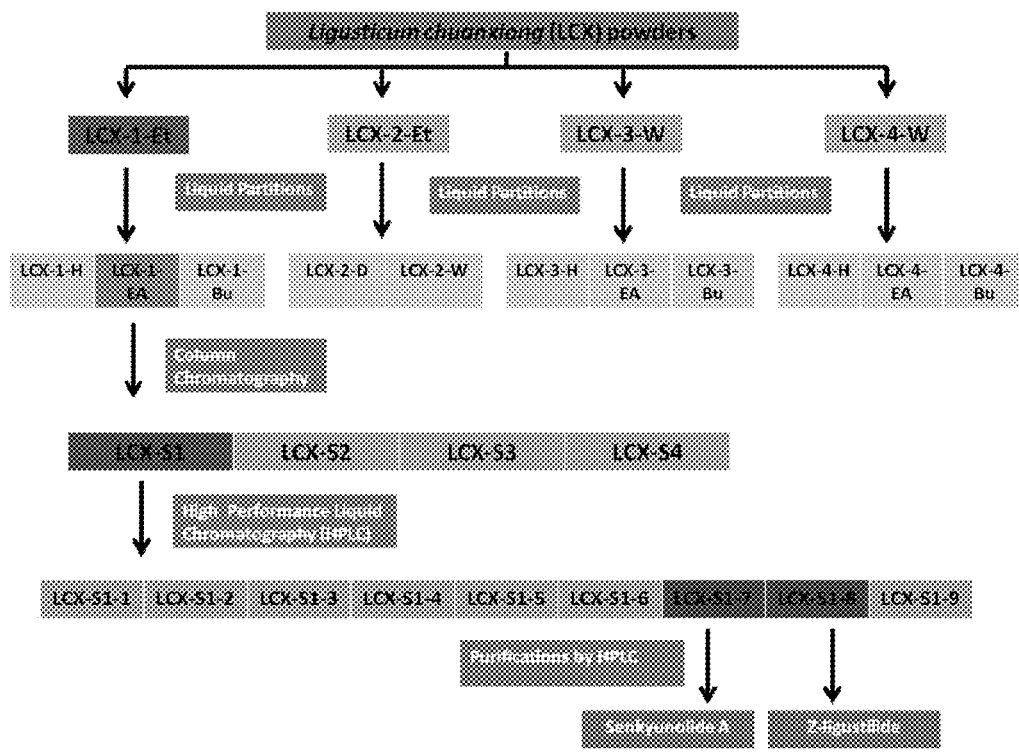
FIG. 1 shows an extraction scheme of bioactive compounds, including senkyunolide A and Z-ligustilide, from *Ligusticum chuanxiong*.

SEQ ID NO:1 is a primer useful according to the subject invention.

SEQ ID NO:2 is a primer useful according to the subject invention.

SEQ ID NO:3 is a primer useful according to the subject invention.

SEQ ID NO:4 is a primer useful according to the subject invention.

DETAILED DESCRIPTION OF THE INVENTION

The subject invention provides novel and advantageous therapeutic methods for treating inflammatory and immune conditions in a subject. In one embodiment, the present invention is useful for treating neuroinflammation and related conditions, cerebrovascular disease and neurodegenerative disease.

The treatment method, which is capable of modulating TNF-α production, comprises administering, to a subject in need of such treatment, an effective amount of an isolated compound having the following formula:

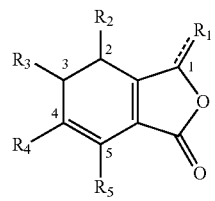

wherein
  ····· represents a carbon-carbon single bond or a carbon-carbon double bond;
  $R_1$ is alkyl or $CR_6$, wherein $R_6$ is alkyl, acyl, haloalkyl, alkylamino or hydroxylalkyl;
  $R_2$, $R_3$ and $R_4$ are, independently, —H, acyl, halo, haloalkyl, amino, alkylamino, hydroxyl, alkyl, hydroxylalkyl, or —COOH; and
  $R_5$ is —H, acyl, halo, haloalkyl, amino, alkylamino, alkyl, hydroxylalkyl, or —COOH.

"Alkyl" means linear saturated monovalent radicals of one to eight carbon atoms or a branched saturated monovalent of three to eight carbon atoms. It may include hydrocarbon radicals of one to four or one to three carbon atoms, which may be linear. Examples include methyl, ethyl, propyl, 2-propyl, n-butyl, iso-butyl, tert-butyl, pentyl, and the like.

"Acyl" means a radical —C(O)R where R is hydrogen, alkyl or cycloalkyl, or heterocycloalkyl. Examples include formyl, acetyl, ethylcarbonyl, and the like.

"Halo" means fluoro, chloro, bromo, or iodo, such as bromo and chloro.

"Haloalkyl" means alkyl substituted with one or more, same or different, halo atoms, e.g., —$CH_2Cl$, —$CH_2Br$, —$CF_3$, —$CH_2CH_2Cl$, —$CH_2CCl_3$, and the like.

"Amino" means the radical —$NH_2$.

"Alkylamino" means a radical —NHR or —$NR_2$ where each R is, independently, an alkyl group. Examples include methylamino, (1-methylethyl)amino, dimethylamino, methylethylamino, di(1-methylethyl)amino, and the like.

"Hydroxy" means the radical —OH.

"Hydroxyalkyl" means an alkyl radical as defined herein, substituted with one or more, preferably one, two or three, hydroxy groups. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxy-propyl, preferably 2-hydroxyethyl, 2,3-dihydroxypropyl and 1-(hydroxymethyl) 2-hydroxyethyl.

An "alkoxy" is intended to mean the radical —$OR_a$, where $R_a$ is an alkyl group. Exemplary alkoxy groups include methoxy, ethoxy, propoxy, and the like.

The subject invention further provides methods for treating inflammatory and immune conditions by administering isolated enantiomeric compounds. The isolated enantiomeric forms of the compounds of the invention are substantially free from one another (i.e., in enantiomeric excess). In other words, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. In one embodiment of the invention, the isolated enantiomeric compounds are at least about in 80% enantiomeric excess. In a preferred embodiment, the compounds are in at least about 90% enantiomeric excess. In a more preferred embodiment, the compounds are in at least about 95% enantiomeric excess. In an even more preferred embodiment, the compounds are in at least about 97.5% enantiomeric excess. In a most preferred embodiment, the compounds are in at least about 99% enantiomeric excess.

The term "subject," as used herein, describes an organism, including mammals such as primates, to which treatment with the compositions according to the present invention can be provided. Mammalian species that can benefit from the disclosed methods of treatment include, but are not limited to, apes, chimpanzees, orangutans, humans, monkeys; and domesticated animals such as dogs, cats, horses, cattle, pigs, sheep, goats, chickens, mice, rats, guinea pigs, and hamsters.

The term "effective amount," as used herein, refers to an amount that is capable of preventing, ameliorating, or treating inflammation or an immune disease or condition. For instance, an effective amount enables at least 5%, 10%, 15%, 20%, 25%, 30%, 35%, 40%, 45%, 50%, 60%, 70%, 80%, 90%, or 100% reduction in TNF-α and/or NO in a test sample of a subject in need of such treatment.

In a specific embodiment, the subject method comprises administering, to a subject, an effective amount of isolated senkyunolide A (Sen A). The chemical structure of senkyunolide A is:

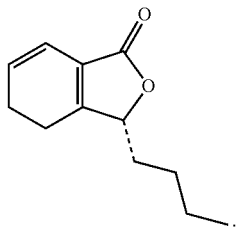

In another specific embodiment, the subject method comprises administering, to a subject, an effective amount of isolated Z-ligustilide (Z-Lig). The chemical structure of Z-ligustilide is:

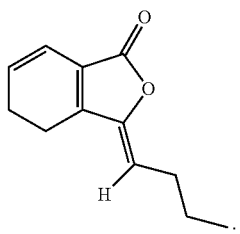

Senkyunolide A and Z-ligustilide can be isolated from *Ligusticum chuanxiong* (Chuanxiong) and its Chinese counterparts using isolation and bioassay-guided procedures as described herein.

In one embodiment, the compounds of the subject invention, including senkyunolide A and Z-ligustilide, are useful for treating neuroinflammation. As shown in the Examples, senkyunolide A and Z-ligustilide suppress the over-production of TNF-α and nitrite in LPS-activated neural cells (e.g., BV-2 cells). Specifically, senkyunolide A suppresses expression of TNF-α and iNOS, and decreases TNF-α mRNA stability in neural cells.

The compounds of the subject invention also protect neuronal cells from damage caused by neuroinflammation during pathogenic activation in microglia, the resident macrophages in the brain. As shown in the Examples, the compounds, such as senkyunolide A and Z-ligustilide, reduce LPS-induced cytotoxicity in neuronal cells. Thus, the compounds of the subject invention are useful as adjunctive therapeutics for stroke and other neuroinflammatory or neurodegenerative diseases.

The anti-inflammatory activity of senkyunolide A is independent of the MAPKs and NF-kB pathways, which are known to be involved in transcriptional regulation of inflammatory mediators triggered by ischemia or LPS[23, 24]. In one embodiment, the compounds of the subject invention, including senkyunolide A and Z-ligustilide, exert their pharmacological action via signaling pathways that involve one or more of the following inflammatory mediators including, activator protein-1 (AP-1), interferon regulatory factor-1 (IRF-1), signal transducer and activator of transcription-1a (STAT-1a), cAMP-responsive element binding protein (CREB), and adenine/uridine rich-element (ARE).

In one embodiment, the subject invention provides therapeutic methods for treating inflammatory and immune conditions by administering an effective amount of senkyunolide A and/or Z-ligustilide to control over-production of TNF-α and nitric oxide. Advantageously, incubation of BV-2 cells with Sen A and Z-Lig at a concentration above 5 μg/ml and 10 μg/ml, respectively, significantly inhibits production of TNF-α under LPS induction. In addition, the subject treatment method is capable of decreasing NO production and TNF-α mRNA stability. Further, the compounds of the subject invention have cytoprotective effects. As shown in Example 7, the application of Z-ligustilide protects cells from apoptotic death during hydrogen peroxide-induced cell injury. In certain embodiments, the compounds of the subject invention reduce the production IL-6, IL-1 and other pro-inflammatory mediators.

In one embodiment, the subject invention provides therapeutic methods for treating inflammatory and immune conditions by administering an effective amount of senkyunolide A and/or Z-ligustilide to modulate one or more of the following inflammatory mediators including, activator protein-1 (AP-1), interferon regulatory factor-1 (IRF-1), signal transducer and activator of transcription-1a (STAT-1a), cAMP-responsive element binding protein (CREB), and adenine/uridine rich-element (ARE).

The methods of the subject invention can also be used to treat inflammation associated with infection, including, but not limited to, infections by viruses, bacteria, fungi, yeast, and other microbes. Additionally, the compounds of the subject invention can be used to treat inflammation mediated by a variety of factors including, but not limited to, interferons, interleukins, and environmental toxins.

Advantageously, the compounds of the subject invention suppress neuroinflammation and protect neuronal cells from death. Thus, the methods of the subject invention are particularly useful for treating treat neuroinflammation and related conditions, cerebrovascular disease, and neurodegenerative disease.

The term "neuroinflammation" or "neuroinflammatory diseases, disorders or conditions," as used herein, includes diseases, disorders and conditions that are associated with the central and peripheral nervous systems, including inflammation that occurs in response to brain injury or autoimmune disorders, and inflammation that causes destruction of healthy neuronal and/or cerebral tissue.

In one embodiment, the compounds of the subject invention can be used to treat neuroinflammation and related conditions, cerebrovascular disease, and neurodegenerative disease including, but not limited to, stroke, ischemic stroke, ischemia, brain ischemia, brain trauma, spinal cord injury, Huntington's disease, Parkinson's disease, multiple sclerosis, Guillain Barre Syndrome, HIV-1-associated dementia (HAD), neuro-AIDS, Creutzfeldt-Jakob Disease, prion disease, brain stem thrombosis and hemorrhage, AIDS-related dementia complex (HIV-related encephalopathy), Devic's disease, Sydenham chorea, Alzheimer's disease, neuropathy, Down's Syndrome, and amyotrophic lateral sclerosis.

In one embodiment, the compounds of the subject invention can be used to treat inflammation caused by concurrent infection or immunological over-reaction to pathogen invasion, including but not limited to inflammation caused by viruses including Varicella zoster (also known as chickenpox or herpes zoster), herpes simplex, cytomegalovirus and herpes simplex virus-8 (also known as AIDS-associated Kaposi sarcoma virus).

In a specific embodiment, the subject invention is used to treat neuralgia or neurasthenia associated with herpes zoster reactivation, commonly known as shingles. In another specific embodiment, the subject invention is used to treat chronic fatigue syndrome caused by viral infections.

In another embodiment, the subject invention is used to treat ischemic stroke, rheumatoid arthritis, psoriasis, cardiovascular disease, cerebrovascular disease, inflammatory bowel disorder, septic shock, and/or graft vs. host rejection.

In one embodiment of the subject invention, a patient who has been diagnosed with a pathological condition is administered a compound or composition of the subject invention. The diagnosis may be made through an appropriate assay, including for example, the detection of a fever. Other assays such as the culturing of tissue or other biological samples to identify pathogens can be used.

In a specific embodiment, the subject method reduces TNF-α and/or nitric oxide production levels and/or destabilizes TNF-α mRNA in cells associated with inflammatory and immune conditions.

In one embodiment, the subject method for treating inflammatory and immune conditions comprises:

(a) determining the presence and/or level of one or more immune system markers in a subject;

(b) administering, to the subject in need of such treatment, an effective amount of an isolated compound having the following formula:

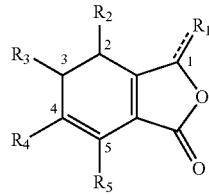

wherein
- - - - - represents a carbon-carbon single bond or a carbon-carbon double bond;

$R_1$ is alkyl or $CR_6$ wherein $R_6$ is alkyl, acyl, haloalkyl, alkylamino or hydroxyalkyl;

$R_2$, $R_3$ and $R_4$ are, independently, —H, acyl, halo, haloalkyl, amino, alkylamino, hydroxyl, alkyl, hydroxylalkyl, or —COOH; and $R_5$ is —H, acyl, halo, haloalkyl, amino, alkylamino, alkyl, hydroxylalkyl, or —COOH; and (c) determining the presence and/or level of one or more immune system markers in the subject; wherein the determination is optionally made at multiple times to monitor the change over time.

In a specific embodiment, the immune system marker(s) is selected from cytokines including TNF-α; NO; interferons such as Interferon-gamma (IFN-γ); the interleukin family such as Interleukin-1 (IL-1), Interleukin-2 (IL-2), Interleukin-3 (IL-3), Interleukin-4 (IL-4), Interleukin-5 (IL-5), Interleukin-6 (IL-6), Interleukin-7 (IL-7), Interleukin-8 (IL-8), Interleukin-9 (IL-9), Interleukin-10 (IL-10), Interleukin-11 (IL-11), Interleukin-12 (IL-12), Interleukin-13 (IL-13), Interleukin-14 (IL-14), Interleukin-15 (IL-15), Interleukin-16 (IL-16), Interleukin-17 (IL-17), Interleukin-18 (IL-18), Interleukin-19 (IL-19), Interleukin-20 (IL-20), Interleukin-21 (IL-21), Interleukin-22 (IL-22), Interleukin-23 (IL-23), Interleukin-24 (IL-24), Interleukin-25 (IL-25), Interleukin-26 (IL-26), Interleukin-27 (IL-27), Interleukin-28 (IL-28), Interleukin-29 (IL-29), Interleukin-30 (IL-30), Interleukin-31 (IL-31), Interleukin-32 (IL-32), Interleukin-33 (IL-33), Interleukin-34 (IL-34), Interleukin-35 (IL-35); the interleukin receptor family; the macrophage inflammatory protein family such as macrophage inflammatory protein 2 (MIP-2) and macrophage inflammatory protein 1α (MIP-1 α); macrophage colony-stimulating factor (M-CSF); monocyte chemotactic protein-1 (MCP-1); and immunoglobulins such as IgA, IgG, IgM, IgD, and IgE.

Immunoglobulins include IgG, IgM, IgD, IgE, IgA and subtypes such as for example IgG1, IgG2, IgG3, IgG4, IgA1, and IgA2. They further include molecules in monomeric or multimeric form, whether digested from whole antibody or produced by other means.

In a further specific embodiment, the immune system marker is selected from the group consisting of TNF-α, NO, IFN-γ, IL-1, IL-2, IL-3, IL-5, IL-4, IL-6, IL-8, IL-10, IL-12, IL-13, IL-14, IL-17, IL-18, IL-23, IL-24, IL-25, IL27, IL-32, G-CSF, M-CSF, MCP-1, MIP-2, MIP-1α, IgA, IgG, IgM, IgD and IgE.

The presence and/or level of the immune system markers can be determined from a sample of biological fluid obtained for the purpose of diagnosis, prognosis, or evaluation of a subject of interest, such as a patient. In certain embodiments, the immune system marker is measured for the purpose of determining the outcome of an ongoing condition or the effect of a treatment regimen on a condition. The immune system marker can be measured in a sample such as, blood, tissue, serum, plasma, urine, saliva, and tears. In one embodiment, the sample is a tissue sample. In one embodiment, the sample is a blood sample. In addition, one of skill in the art would realize that some samples would be more readily analyzed following a fractionation or purification procedure, for example, separation of whole blood into serum or plasma components.

In a further embodiment, the immune system marker can be determined by quantitative immunological detection methods, such as for example, enzyme-linked immunosorbant assay (ELISA), western blot, immunological assays, microarray, and radioimmunoassay.

Further, a plurality of markers can be measured. In addition, analysis of a plurality of markers may be carried out separately or simultaneously. Several markers may be combined into one test for efficient processing of multiple samples from a subject.

In addition, the presence and/or level of one or more markers can be determined multiple times over time to monitor the change of a subject's conditions. Such testing of multiple samples allows for the identification of changes in the marker over time. Increases or decreases in the marker, as well as the absence of change in levels, would provide useful information about the disease status that includes, but is not limited to, identifying the approximate time from onset of the event, the appropriateness of the subject therapy, the effectiveness of the subject therapy, identification of the severity of the event, identification of the disease severity, and identification of a future outcome.

In addition, the method of the present invention can be used in the treatment, or amelioration, of inflammatory symptoms in any disease, condition or disorder where immune and/or inflammation suppression is beneficial. Inflammatory diseases, conditions or disorders in which the compounds and compositions of the present invention can be used to inhibit include, but are not limited to, unwanted immune reactions and inflammation including, but not limited to, arthritis (e.g., rheumatoid arthritis), ischemic stroke, and other diseases, conditions or disorders of the joints or musculoskeletal system in which immune and/or inflammation suppression is beneficial.

Moreover, the subject method is also useful to treat or ameliorate inflammation associated with atherosclerosis; arteriosclerosis; atherosclerotic heart disease; reperfusion injury; cardiac arrest; myocardial infarction; vascular inflammatory disorders including cerebro-vascular disease (stroke); respiratory distress syndrome and other cardiopulmonary diseases, conditions or disorders where immune and/or inflammation suppression would be beneficial.

In addition, the subject method is also useful to treat or ameliorate inflammation associated with peptic ulcer; ulcerative colitis, Crohn's Disease, irritable bowel syndrome, other inflammatory bowel conditions, and other diseases, conditions or disorders of the gastrointestinal tract where immune inflammation suppression would be beneficial; hepatic fibrosis; liver cirrhosis and other hepatic diseases, conditions or disorders where immune and/or inflammation suppression would be beneficial; thyroiditis and other glandular diseases, conditions or disorders where immune and/or inflammation suppression would be beneficial; glomerulonephritis and other renal and urologic diseases, conditions or disorders where immune and/or inflammation suppression would be beneficial.

In addition, the subject method is useful to treat or ameliorate inflammation associated with post-traumatic inflammation; septic shock; infectious diseases where immune and/or inflammation suppression would be beneficial; inflammatory complications and side effects of surgery where immune and/or inflammation suppression would be beneficial; bone marrow transplantation and other transplantation complications and/or side effects where immune and/or inflammation suppression would be beneficial; inflammatory and/or immune complications and side effects of gene therapy, e.g., due to infection with a viral carrier; and inflammation associated with acquired immune deficiency syndrome (AIDS).

Further, the subject method is also useful to inhibit macrophage or T cell associated aspects of an immune response that are not associated with inflammation. The compounds and compositions are able to inhibit macrophage or T cell activities including, but not limited to, macrophage antigen-presenting activity, macrophage cytokine production, T cell cytokine production, T cell adhesion activity, T cell proliferation, etc. Thus, the compounds and compositions are useful to suppress or inhibit a humoral and/or cellular immune response.

The subject method is also useful to treat or ameliorate monocyte and leukocyte proliferative diseases, e.g., leukemia, by reducing the amount of monocytes and lymphocytes.

The subject method is further useful for the prevention and/or treatment of graft rejection in cases of transplantation of natural or artificial cells, tissue and organs, such as cornea, bone marrow, organs, lenses, pacemakers, natural and artificial skin tissue, and the like.

The subject method is also useful to treat or ameliorate inflammation associated with hypersensitivity; allergic reactions; asthma; systemic lupus erythematosus; collagen diseases and other autoimmune diseases such as multiple sclerosis, conditions or disorders in which immune and/or inflammation suppression is beneficial.

The subject method is also useful to treat or ameliorate inflammation associated with otitis and other otorhinolaryngological diseases, conditions or disorders where immune and/or inflammation suppression would be beneficial; dermatitis and other dermal diseases, conditions or disorders where immune and/or inflammation suppression would be beneficial; periodontal diseases and other dental diseases, conditions or disorders where immune and/or inflammation suppression would be beneficial.

In addition, the subject method also is useful to treat or ameliorate inflammation associated with herpes zoster (shingles); posterior uveitis; intermediate uveitis; anterior uveitis; conjunctivitis; chorioretinitis; uveoretinitis; optic neuritis; intraocular inflammation, such as retinitis and cystoid macular edema; sympathetic ophthalmia; scleritis; retinitis pigmentosa; immune and inflammatory components of degenerative fondus disease; inflammatory components of ocular trauma; ocular inflammation caused by infection; proliferative vitreoretinopathies; acute ischemic optic neuropathy; excessive scarring, for example, following glaucoma filtration operation; immune and/or inflammation reaction against ocular implants and other immune and inflammatory-related ophthalmic diseases, conditions or disorders where immune and/or inflammation suppression would be beneficial.

Moreover, the subject method is also useful to treat or ameliorate inflammation associated with autoimmune diseases and conditions or disorders where, both in the central nervous system (CNS) and in any other organ, immune and/or inflammation suppression would be beneficial; Parkinson's disease; complications and/or side effects from treatment of Parkinson's disease; AIDS-related dementia complex (HIV-related encephalopathy); Devic's disease; Sydenham chorea; Alzheimer's disease and other degenerative diseases, conditions or disorders of the central nervous system where immune and/or inflammation suppression would be beneficial; inflammatory components of strokes; post-polio syndrome; immune and inflammatory components of psychiatric disorders; myelitis; encephalitis; subacute sclerosing panencephalitis; encephalomyelitis; acute neuropathy; subacute neuropathy; chronic neuropathy; Guillain-Barre syndrome; myasthenia gravis; pseudotumor cerebri; Down's Syndrome; Huntington's disease; amyotrophic lateral sclerosis; inflammatory components of central nervous system (CNS) compression or CNS trauma or cerebrovascular accidents (stroke) or infections or hypoxia-ischemia of the CNS; inflammatory components of muscular atrophies and dystrophies; and immune and inflammatory related diseases, conditions or disorders of the central and peripheral nervous systems where immune and/or inflammation suppression would be beneficial.

In yet another embodiment, the subject method is useful to restore immune privilege at an immune privileged site which has lost its immune privilege such as brain, eye and testis.

In one embodiment, the subject invention provides a therapeutic method by administering isolated compounds. As used herein, "isolated" refers to compounds that have been removed from any environment in which they may exist in nature. For example, isolated Sen A or isolated Z-Lig would not refer to the Sen A compound or the Z-Lig compound as it exists in *Ligusticum chuanxiong*. In preferred embodiments, the compounds of the subject invention are at least 75% pure, preferably at least 90% pure, more preferably are more than 95% pure, and most preferably are more than 99% pure (substantially pure).

The present invention also provides for a therapeutic method by administering therapeutic or pharmaceutical compositions in a form that can be combined with a pharmaceutically acceptable carrier. In this context, the compound may be, for example, isolated or substantially pure. The term "carrier" refers to a diluent, adjuvant, excipient, or vehicle with which the compound is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers, particularly for injectable solutions. Particularly preferred pharmaceutical carriers for treatment of or amelioration of inflammation in the central nervous system are carriers that can penetrate the blood/brain barrier. As used herein carriers do not include the natural plants as they exist in nature.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The therapeutic composition, if desired, can also contain minor amounts of wetting or emulsifying agents, or pH buffering agents. These compositions can take the form of solutions, suspensions, emulsion, tablets, capsules, powders, sustained-release formulations and the like. The composition can be formulated with traditional binders and carriers such as triglycerides. Examples of suitable pharmaceutical carriers are described in "Remington's Pharmaceutical Sciences" by E. W. Martin. Such compositions contain a therapeutically effective amount of the therapeutic composition, together with a suitable amount of carrier so as to provide the form for proper administration to the patient. The formulation should suit the mode of administration.

In one embodiment, the composition is formulated in accordance with routine procedures as a pharmaceutical composition adapted for local injection administration to human beings. Typically, compositions for local injection administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is administered by injection, an ampoule of sterile water for injection or saline can be provided so that the ingredients may be mixed prior to administration.

The therapeutic or pharmaceutical compositions of the invention can be formulated as neutral or salt forms. Pharmaceutically acceptable salts include those derived from hydrochloric, phosphoric, acetic, oxalic, tartaric acids, sodium, potassium, ammonium, calcium, ferric hydroxides, isopropylamine, triethylamine, 2-ethylamino ethanol, etc.

The present invention also provides for the modification of the compound such that it is more stable once administered to a subject, i.e., once administered it has a longer time period of effectiveness as compared to the unmodified compound. Such modifications are well known to those of skill in the art, e.g., microencapsulation, etc.

The amount of the therapeutic or pharmaceutical composition of the invention which is effective in the treatment of a particular disease, condition or disorder will depend on the nature of the disease, condition or disorder and can be determined by standard clinical techniques. In general, the dosage ranges from about 0.001 mg/kg to about 2 mg/kg.

For instance, suitable unit dosages may be between about 0.01 to about 5 mg, about 0.01 to about 4 mg, about 0.01 to about 3 mg, about 0.01 to about 2 mg, about 0.01 to about 1 mg, about 0.01 to about 500 µg, about 0.01 to about 400 µg, about 0.01 to about 300 µg, about 0.01 to about 200 µg, about 0.01 to about 100 µg, or about 0.01 to about 50 µg. Such a unit dose may be administered more than once a day, e.g. two or three times a day.

In addition, in vitro assays may optionally be employed to help identify optimal dosage ranges. The precise dose to be employed in the formulation will also depend on the route of administration, and the seriousness of the disease, condition or disorder, and should be decided according to the judgment of the practitioner and each patient's circumstances. Effective doses may be extrapolated from dose-response curves derived from in vitro or animal model test systems. For example, in order to obtain an effective mg/kg dose for humans based on data generated from rat studies, the effective mg/kg dosage in rats is divided by six.

The invention also provides a pharmaceutical pack or kit comprising one or more containers filled with one or more of the ingredients, e.g., compound, carrier suitable for administration.

The method of administration can also be practiced consistent with traditional Chinese medicine practices. The composition and dosage of the formulation that are effective in the treatment of a particular disease, condition or disorder will depend on the nature of the disease, condition or disorder by standard clinical techniques.

The traditional Chinese medicine in prescription amounts can be readily made into any form of drug, suitable for administering to humans or animals. Suitable forms include, for example, tinctures, decoctions, and dry extracts. These can be taken orally, applied through venous injection or mucous membranes. The active ingredient can also be formulated into capsules, powder, pallets, pastille, suppositories, oral solutions, pasteurized gastroenteric suspension injections, small or large amounts of injection, frozen powder injections, pasteurized powder injections and the like. All of the above-mentioned methods are known to people skilled in the art, described in books and commonly used by practitioners of herbal medicine.

A tincture is prepared by suspending herbs in a solution of alcohol, such as, for example, wine or liquor. After a period of suspension, the liquid (the alcohol solution) may be administered for example, two or three times a day, one teaspoon each time.

A decoction is a common form of herbal preparation. It is traditionally prepared in a clay pot, but can also be prepared in glass, enamel or stainless steel containers. The formulation can be soaked for a period of time in water and then brought to a boil and simmered until the amount of water is reduced by, for example, half.

An extract is a concentrated preparation of the essential constituents of a medicinal herb. Typically, the essential constituents are extracted from the herbs by suspending the herbs in an appropriate choice of solvent, typically, water, ethanol/water mixture, methanol, butanol, iso-butanol, acetone, hexane, petroleum ether or other organic solvents.

The extracting process may be further facilitated by means of maceration, percolation, repercolation, counter-current extraction, turbo-extraction, or by carbon-dioxide hypercritical (temperature/pressure) extraction. After filtration to rid of herb debris, the extracting solution may be further evaporated and thus concentrated to yield a soft extract (extractum spissum) and/or eventually a dried extract (extractum siccum), by means of spray drying, vacuum oven drying, fluid-bed drying or freeze-drying. The soft extract or dried extract may be further dissolved in a suitable liquid to a desired concentration for administering or processed into a form such as pills, capsules, injections, etc.

Materials and Methods

Chemicals and Antibodies

Endotoxin (lipopolysachamide, LYS) from *E. coli* was purchased from Sigma and used as an inducer of TNF-α expression. All of the chemical solvents were purchased from Merck (Darmstadt, Germany). The antibodies against the phospho-MAPKs were obtained from Cell Signaling Technology (Beverly, Mass.). The antibodies against NF-kB p65 and actin were purchased from Santa Cruz Technology (Santa Cruz, Calif.). Anti-rabbit and anti-mouse IgG HRP-conjugated secondary antibodies were purchased from BD Biosciences (San Diego, Calif.), while anti-goat IgG HRP-conjugated secondary antibodies were purchased from ZYMED Laboratory Inc (South San Francisco, Calif.).

Cell Culture and Primary Blood Macrophage Isolation

Murine microglia cell line BV-2, commonly used for microglial research[25], is maintained in Dulbecco's modified Eagle's minimum essential medium (DMEM) supplemented with 10% FBS and 1% penicillin and streptomycin (Invitrogen Life Technologies) at 37° C. in a humidified atmosphere with 5% $CO_2$ in warm air.

Neuro-2a, a murine neuroblastoma cell line, was obtained from American Type Culture Collection (ATCC Accession No. CCL-131). It was maintained in Eagle's Minimum Essential Medium (MEM) supplemented with 10% FBS and 1% Penicillin and Streptomycin (Invitrogen Life Technologies, Carlsbad, Calif.). The cells were cultured at 37° C. in a humidified atmosphere of 5% CO2.

PC-12 cells derived from a transplantable rat pheochromocytoma were obtained from American Type Culture Collection (ATCC Accession No. CRL-1721.1). The cells were maintained in F-12K Medium supplemented with 15% horse serum, 2.5% FBS, 1% penicillin, and streptomycin (Invitrogen Life Technologies, Carlsbad, Calif.) at 37° C. in a humidified atmosphere of 5% $CO_2$.

Human peripheral blood macrophages cells (PBMac) were used in the cytotoxicity screening and for the verification of the effects of senkyunolide A and Z-ligustilide. Recent reports showed that blood monocytes/macrophages can be used as a relevant model to study neuroinflammation and pathogenesis of neurodegenerative diseases because they share many common surface receptors and signaling proteins with microglia. Blood monocytes/macrophages response similar to microglial cells during the pathogenesis of neurodegenerative diseases[26].

Human peripheral blood macrophages cells (PBMac) were isolated from the buffy coat of healthy donor blood supplied by Hong Kong Red Cross by Ficoll-Paque (GE Healthcare) density gradient centrifugation as described in our previous reports[14,15]. In brief, the buffy coat was spun at 3000 rotations per minute (rpm) for 15 minutes to separate the blood cells from the plasma. The heat inactivated serum was filtered for future use.

The cell layer was diluted with phosphate buffered saline (PBS) in a ratio of 1:1. The diluted cells were overlaid on Ficoll-Paque slowly and centrifuged at 2300 rpm for 20 minutes for separation of mononuclear cells from erythrocytes. The mononuclear cell layer was removed and washed with RPMI 1640 medium until the supernatant was clear.

The cells were finally resuspended in RPMI 1640 medium supplemented with 5% autologous serum and cultured for 1 hour. The non-adherent cells were removed afterwards and the remaining adherent cells were further incubated for another 24 hours at 37° C. in 5% carbon dioxide ($CO_2$).

The adherent monocytic cells were detached and seeded onto tissue culture plates and incubated for another 7-14 days in order to differentiate the primary blood monocytic cells to primary blood macrophages (PBMac).

Total RNA Extraction

Total RNA was extracted using TRIzol reagent (Invitrogen Life Technologies, Carlsbad, Calif.) according to the manufacturer's instructions and described in our previous studies[27].

Polymerase Chain Reaction (PCR) and Real-Time RT-PCR

Semi-quantitative PCR assays of targeted genes were performed in a 25 μl reaction mixture containing 1.5 mM $MgCl_2$, 0.2 mM of each deoxynucleoside triphosphate, 0.25 μM of each primer, 2 units of Taq polymerase (GE Healthcare), and 1 μl of cDNA. PCR primer sets for TNF-α and glyceraldehyde-3-phosphate dehydrogenase (GAPDH) were as follows. TNF-α (upstream: 5'-GGCTCCAGGCGGTGCT TGTCC-3' (SEQ ID NO:1); downstream: 5'-AGACGGC-GATGCGGCTGATG-3' (SEQ ID NO:2)), and GAPDH (upstream: 5'-ACCACAGTCCATGCCATCAC-3' (SEQ ID NO:3); downstream: 5'-TCCACCACCCTGTTGCTGTA-3' (SEQ ID NO:4). The thermal cycling condition for PCR was 94° C. for 30 s, 60° C. for 30 s, and 72° C. for 1 min. The cycling reactions were repeated for 24 more cycles.

The levels of TNF-α mRNA and iNOS mRNA were determined by real-time RT-PCR (Roche 480II). 18S ribosomal RNA (18S) was used as an internal control. All of the real-time RT-PCR probes were obtained from the Universal Probe Library (Roche). All of the samples were performed in duplicate. The number of $C_T$ of the targeted gene was normalized to that of the 18S in each sample ($\Delta C_T$). The mRNA expression levels of the samples were relative to the mock-treated samples ($\Delta\Delta C_T$). The relative mRNA expression of the targeted genes was calculated by $2^{-\Delta\Delta C_T}$ and expressed as fold induction.

Nitrite Measurement

Nitrite levels in the culture media were determined using Griess reagent under manufacturer's instructions (Sigma Aldrich, St. Louis, Mo.). Fresh culture media were used as blanks and the nitrite levels were determined by using a standard sodium nitrite curve.

Enzyme-Linked Immunosorbent Assay (ELISA)

To measure the TNF-α level in cell culture supernatants, BV-2 cells were seeded at $1\times10^5$ cells/ml in the volume of 0.5 ml in 24-well culture plates. They were co-treated with or without 100 ng/ml LPS in the absence or presence of indicated concentrations of bioactive compounds of LCX for 18 h. In addition, PBMac cells were seeded at $1\times10^6$ cells/ml in the volume of 0.5 ml in 24-well plates. After incubation, the supernatants were collected and TNF-α levels were determined by ELISA according to the manufacturer's instructions (R&D Systems).

MTT Assay for Cell Viability

Cell viability and cytotoxicity of the fractions of the LCX were assessed using MTT assay. PC-12 cells ($2.5\times10^4$ cells/ml), PBMac cells ($5\times10^5$ cells/ml), and BV-2 cells ($5\times10^4$ cells/ml), were seeded in 24-well culture plates, respectively. PC-12 cells were treated with Z-ligustilide, followed by treatment with hydrogen peroxide for the indicated time periods. The treated cells were incubated with 0.5 mg/ml MTT solution (Sigma Aldrich, St. Louis, Mo.) for 1 h at 37° C. The medium was discarded and 200 µl isopropyl alcohol (IPP) was then added. After 15 min of incubation, the absorbance was measured at 570 nm.

Conditioned Culture Medium Transfer Model

BV-2 cells were seeded at $3\times10^5$ cells/ml in 12-well culture plates (1 ml in each well). They were co-treated with or without 100 ng/ml LPS, in the presence of 0.05% DMSO, 50 µg/ml senkyunolide A, or 50 µg/ml Z-ligustilide, for 18 h. The supernatants were then collected and centrifuged at 13,200 rpm for 3 min. The resulting supernatants were then transferred to Neuro-2a cells ($1\times10^5$ cells/ml in 24-well culture plates), which were incubated for another 48 h. Cell viability of Neuro-2a cells was measured by MTT assay.

Western Blot $10^5$ cells/ml BV-2 cells were first pretreated with senkyunolide A for 1 h. After induction by 100 ng/ml LPS for 30 min, the culture medium was discarded. Cytoplasmic proteins and nuclear proteins were extracted separately by buffer A and buffer C as described in our previous report[28]. The cell lysates were separated by 10% SDS-polyacrylamide gel electrophoresis and transferred to a nitrocellulose membrane (Schleicher & Schuell, Germany). The cell lysates were incubated with specific antibodies (phospho-MAP kinases, Actin, NF-kB p65 and Lamin B) overnight. After three washes, the membranes were incubated with the corresponding secondary antibodies. The bands were detected using the Enhanced Chemiluminescence System (GE Healthcare, Piscataway, N.J., USA) according to the manufacturer's instructions.

TNF-α mRNA Stability Assays $10^5$ BV-2 cells were first stimulated by 100 ng/ml LPS. After 2 h of LPS treatment, transcription inhibitor actinomycin D (Act D) at a concentration of 1 ug/ml was added to stop the mRNA synthesis. Total RNA was harvested at indicated time points after actinomycin D treatment (post-Act D). The level of TNF-α mRNA was measured by real-time quantitative RT-PCR.

Statistical Analysis

Student's t-test was used to determine statistical significance between the experimental and control groups. All experimental data are expressed as the mean value±standard deviation. A p value <0.05 was used as an indicator of statistical significance.

EXAMPLES

Following are examples that illustrate procedures for practicing the invention. These examples should not be construed as limiting.

Example 1

Extraction and Isolation of Bioactive Compounds from *Ligusticum chuanxiong*

*Ligusticum chuanxiong* (LCX) obtained from Purapharm International (H.K.) Ltd. is ground into powder. Methods for extracting bioactive compounds are shown in FIG. 1 and illustrated as follows.

In the first method, LCX powders are soaked in 95% ethanol at room temperature with continuous sonication for 30 minutes. After the extract is concentrated using a Rotavapor (Büchi), it is suspended in water and then partitioned sequentially with hexane, ethyl acetate and then butanol. Three fractions, namely LCX-1-Et-H, LCX-1-Et-EA and LCX-1-Et-Bu, are obtained.

In the second method, LCX powders are heated in 70% ethanol under continuous reflux for 30 minutes. After the extract is concentrated using a Rotavapor (Büchi), it is suspended in water, and partitioned with dichloromethane (DCM). Two fractions, namely LCX-2-Et-D (the DCM fraction) and LCX-2-Et-W (the water faction), are obtained.

In the third method, LCX powders are boiled in water for 30 minutes. After the extract is concentrated using a Rotavapor (Büchi), it is partitioned sequentially with hexane, ethyl acetate and then butanol. Three fractions, namely LCX-3-W-H, LCX-3-W-EA and LCX-3-W-Bu, are obtained.

In the fourth method, LCX powders are soaked in water at room temperature with continuous sonication for 30 minutes. After the extract is concentrated using a Rotavapor (Büchi), it is partitioned sequentially with hexane, ethyl acetate and then butanol. Three fractions, namely LCX-4-W-H, LCX-4-W-EA and LCX-4-W-Bu, are obtained.

Example 2

Effect of Bioactive Extracts on Nitric Oxide Production

The effect of each extract on nitric oxide production is evaluated according to the procedures illustrated as follows. Briefly, murine microglia cell line BV-2 is maintained in Dulbecco's modified Eagle's minimum essential medium (DMEM) supplemented with 10% FBS and 1% penicillin and streptomycin (Invitrogen Life Technologies, Carlsbad, Calif.) at 37° C. in a humidified atmosphere with 5% $CO_2$ in warm air.

0.1 M cells/ml BV-2 cells are seeded in 24-well plates (0.5 ml in each well). Cells are treated with 0.05% DMSO; 0.05% DMSO and 100 ng/ml LPS; or 100 ng/ml LPS and 50 µg/ml of an LCX extract for 18 hours, respectively. The culture supernatant is collected. The nitric oxide level is measured using the Griess reagent according to standard manufacturer's instructions (Sigma Aldrich, St. Louis, Mo.), and assessed using the standard sodium nitrite curve.

The results reveal that LCX-1-Et-EA extract inhibits nitrite production in BV-2 cells. The LCX-1-Et-EA extract is subjected to additional column chromatography. The extract is further purified by reversed-phase high-performance liquid chromatography (HPLC) using a reversed-phase column Econosphere C18 10u (250×22 mm ID), with a detection wavelength at 210 nm and a gradient elution at a flow of 6 ml $min^{-1}$ consisting of solvents (A) water and (B) acetonitrile of the following concentration: 0-15 min, 50%-90% B; 16-20 min, 90% B; and 21-35 min, 50% B.

Figure 2A:
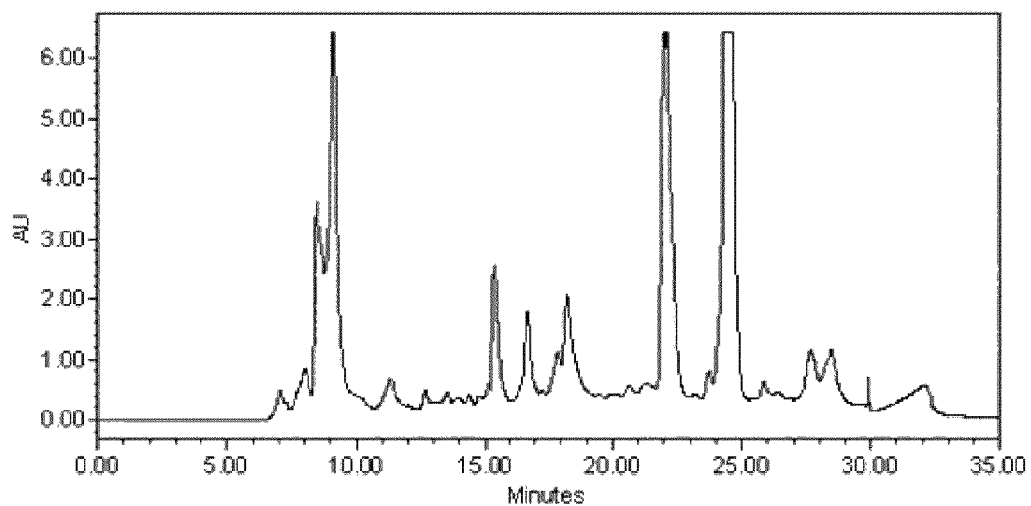
FIG. 2A-B show high performance liquid chromatography (HPLC) chromatograms of subfractions separated from the extract LCX-1-Et-EA-S1.
Figure 2B:
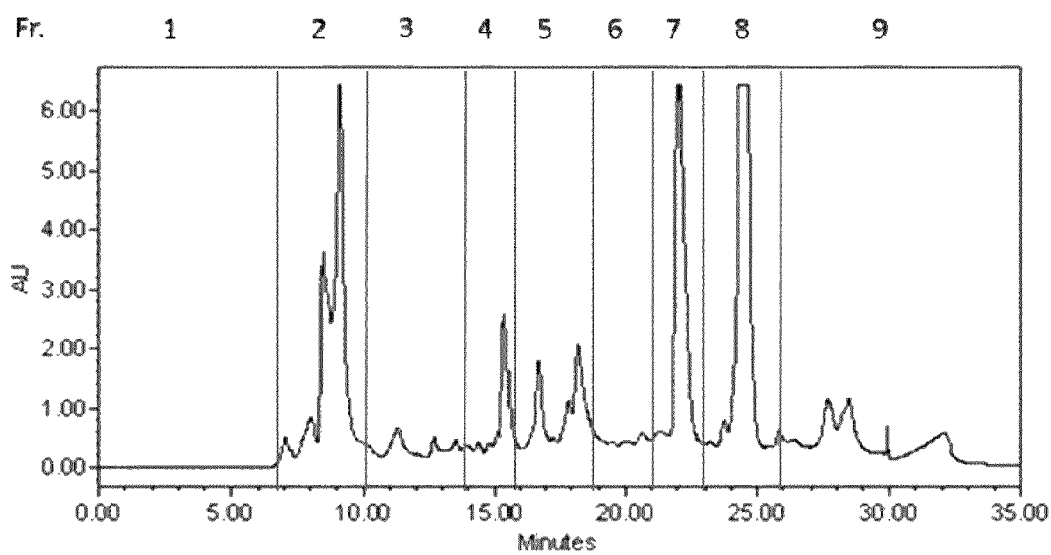

Using the chromatographic conditions described as above, LCX-1-Et-EA-S1 is separated into 9 fractions as shown in FIGS. 2a) and 2b). Nine fractions are obtained, including LCX-1-Et-EA-S1-1 (S1-1), LCX-1-Et-EA-S1-2 (S1-2), LCX-1-Et-EA-S1-3 (S1-3), LCX-1-Et-EA-S1-4 (S1-4), LCX-1-Et-EA-S1-5 (S1-5), LCX-1-Et-EA-S1-6 (S1-6), LCX-1-Et-EA-S1-7 (S1-7), LCX-1-Et-EA-S1-8 (S1-8), and LCX-1-Et-EA-S1-9 (S1-9).

Figure 3:
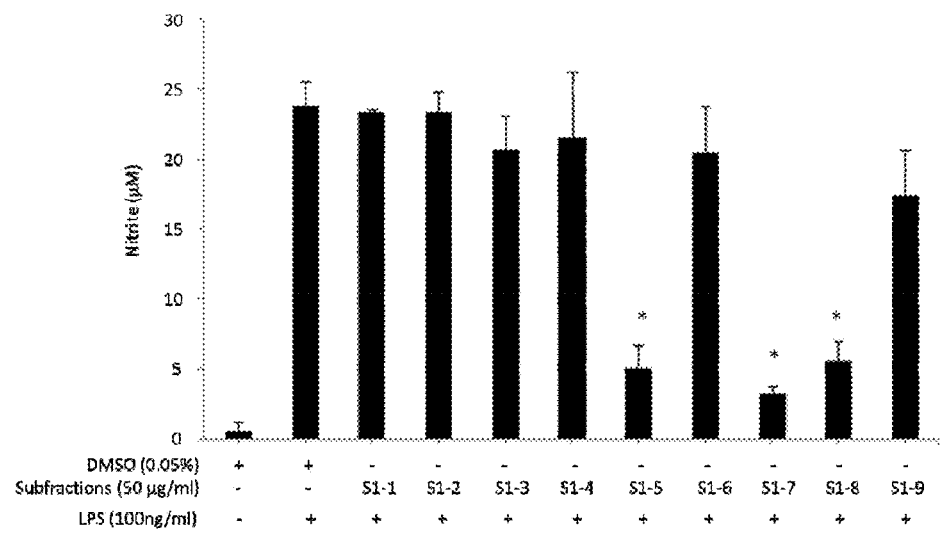
FIG. 3 shows the effect of subfractions separated from LCX-1-Et-EA-S1 on nitrite production in BV-2 cells. ($p<0.05$, compared with DMSO+LPS only).

The effect of S1-1-S1-9 on nitrite production in BV-2 cells is further evaluated using the same procedure as illustrated above. The results, as shown in FIG. 3, reveal that S1-5, S1-7, and S1-8 significantly inhibit nitrite production. Specifically, S1-7 and S1-8 successfully inhibit nitrite production by 6-fold and 4-fold, respectively. Two bioactive compounds were isolated and purified by HPLC with purity >95%.

The bioactive compounds of S1-7 and S1-8 are identified by gas chromatography mass spectrometry (GC: Agilent, 7890A, MS: Agilent, 5975C) using a HP-5MS column (25 m×350 µm). The oven temperature starts at 70° C. for 1 min, and then increases to 180° C. at a rate of 10° C./min. After holding for 2 min, the temperature increases from 180° C. to 280° C. at a rate of 10° C./min and it is held at 280° C. for 3 min. The injection temperature is 275° C. Helium is used as the carrier gas at a flow of 1 ml/min. By using GC/MS, the mass to charge ratio of the compounds was determined as 192.2 and 190.2, respectively. The structures of pure compounds S1-7 and S1-8 are elucidated based on their mass spectrometric fragmentation patterns. It reveals that the bioactive compound of S1-7 is senkyunolide A (Sen A) and the bioactive compound of S1-8 is Z-ligustilide (Z-Lig).

Example 3

Effect of Senkyunolide A and Z-Ligustilide on LPS-Induced Nitric Oxide Production The effect of senkyunolide A (Sen A) and Z-ligustilide (Z-Lig) at various concentrations on LPS-induced nitrite production is further evaluated in this Example. Briefly, 0.1 M cells/ml BV-2 cells are seeded in 24-well plates (0.5 ml in each well). Cells are treated with 0.05% DMSO; 0.05% DMSO and 100 ng/ml LPS; 50 µg/ml Sen A/Z-Lig; or 100 ng/ml LPS and Sen A/Z-Lig at a concentration of 1 µg/ml, 5 µg/ml, 10 µg/ml, 25 µg/ml, and 50 µg/ml for 18 hours, respectively. The culture supernatant is collected. The nitric oxide level is measured using the Griess reagent according to standard manufacturer's instructions (Sigma Aldrich, St. Louis, Mo.), and evaluated using the standard sodium nitrite curve.

Figure 4:
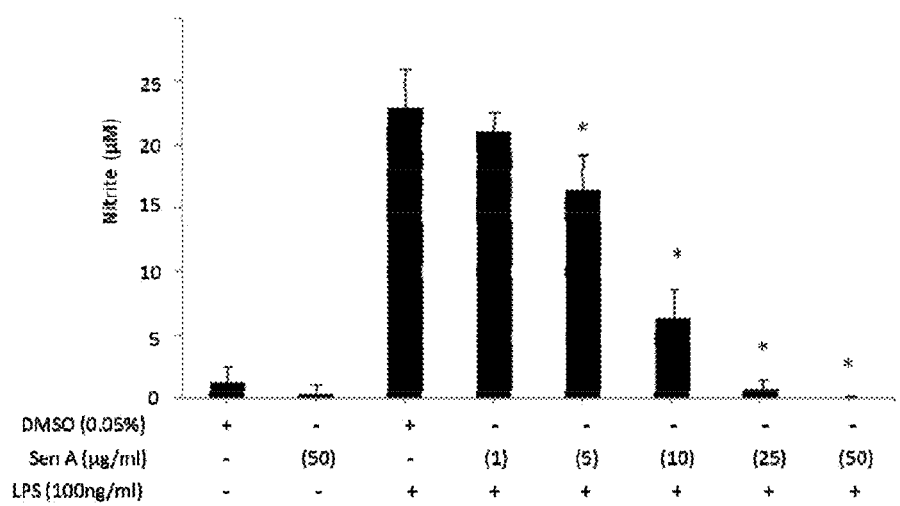
FIG. 4 shows the dose-dependent effect of senkyunolide A on nitrite production in BV-2 cells. ($p<0.05$, compared with DMSO+LPS only).
Figure 5:
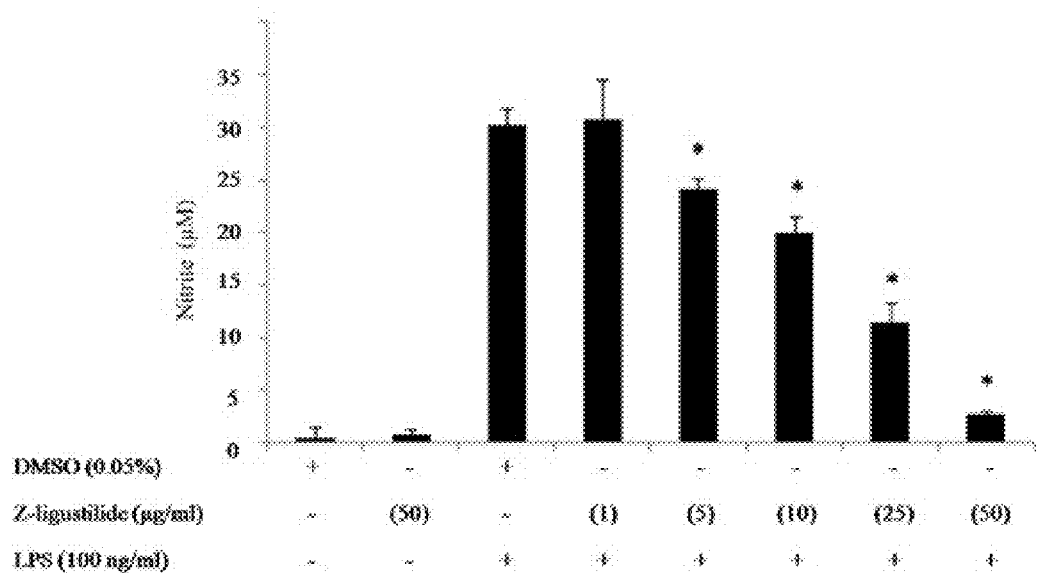
FIG. 5 shows the dose-dependent effect of Z-ligustilide on nitrite production in BV-2 cells. ($p<0.05$, compared with DMSO+LPS only).

The results, as shown in FIGS. 4 and 5, reveal that the application of either Sen A or Z-Lig at a concentration of above 5 µg/ml significantly inhibits nitrite production. Specifically, Sen A at a concentration of 10 µg/ml and 25 µg/ml produces an approximately 4-fold and 20-fold reduction in nitrite production, respectively. More significantly, Sen A at a concentration of 50 µg/ml almost completely inhibits nitrite production. Z-ligustilide also inhibits nitrite production in a dose-dependent manner (FIG. 5).

Example 4

Effect of Senkyunolide A and Z-Ligustilide on TNF-α Production

This Example shows that senkyunolide A and Z-ligustilide inhibit TNF-α production induced by LPS in a dose-dependent manner. To study the effect of Sen A and Z-Lig at various concentrations on TNF-α production, $1 \times 10^6$ cells/ml (FIG. 6) PBMac cells are seeded in 24-well plates (0.5 ml in each well). Cells are treated with 25 µg/ml or 50 µg/ml Sen A, Z-Lig, or DMSO for 24 hours prior to the addition of 1 ng/ml LPS, and further incubated for another 24 hours. The culture supernatants are collected and the level of secreted TNF-α is measured by ELISA according to the manufacturer's instructions (R&D Systems, Minneapolis, Minn.).

Figure 6:
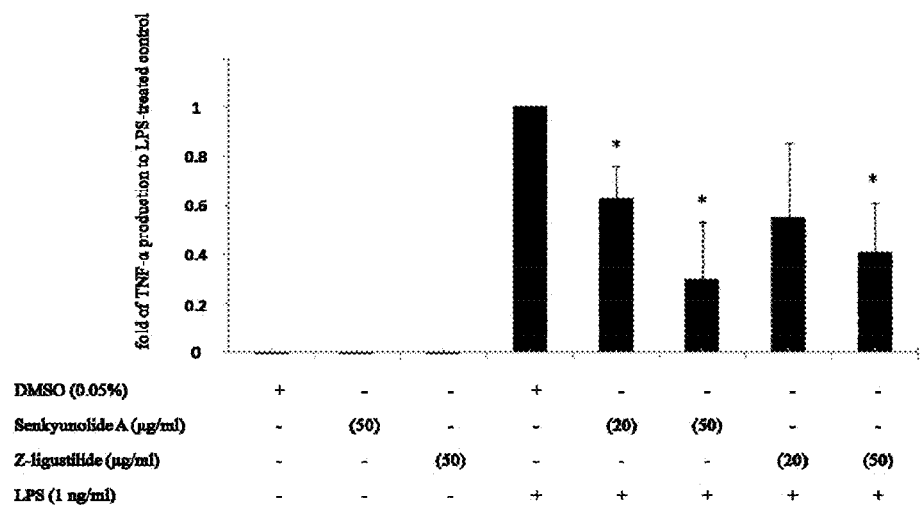
FIG. 6 shows the effect of senkyunolide A and Z-ligustilide on TNF-α production in human blood macrophages. ($p<0.05$, compared with DMSO+LPS only).

The results, as shown in FIG. 6, reveal that Sen A and Z-Lig suppress endotoxin-induced TNF-α production in a dose-dependent manner.

Example 5

Effect of Senkyunolide A and Z-Ligustilide on TNF-α Production

The role of senkyunolide A (Sen A) and Z-ligustilide (Z-Lig) in suppressing TNF-α production is further evaluated in this Example. Briefly, $5 \times 10^4$ cells/ml BV-2 cells are seeded in 24-well plates (0.5 ml in each well). Cells are treated with 0.05% DMSO; 0.05% DMSO and 100 ng/ml LPS; 50 µg/ml Sen A/Z-Lig; or 100 ng/ml LPS and Sen A/Z-Lig at a concentration of 1 µg/ml, 5 µg/ml, 10 µg/ml, 25 µg/ml, and 50 µg/ml for 18 hours, respectively. The culture supernatant is collected and the level of secreted TNF-α is measured by ELISA.

Figure 7:
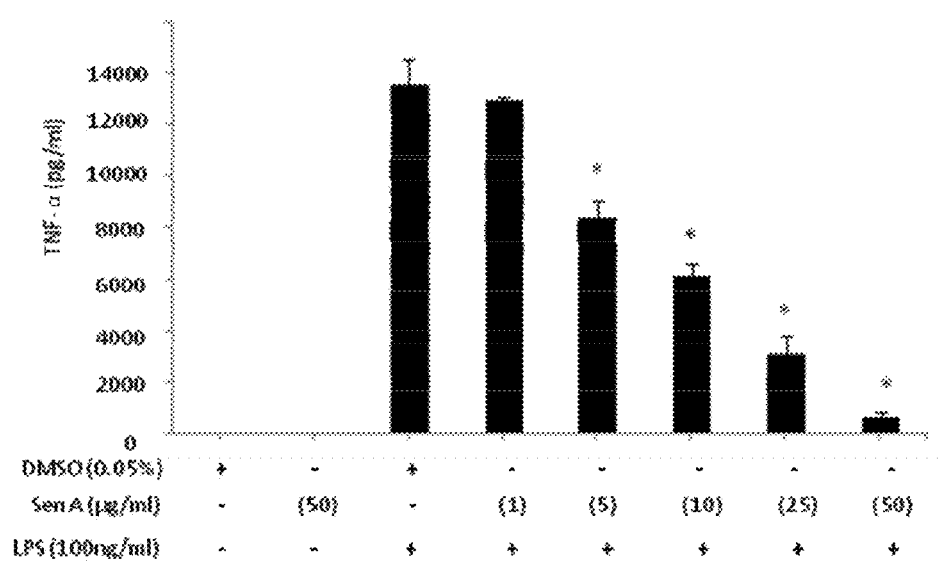
FIG. 7 shows the dose-dependent effect of senkyunolide A on TNF-α protein production in BV-2 cells. ($p<0.05$, compared with DMSO+LPS only).
Figure 8:
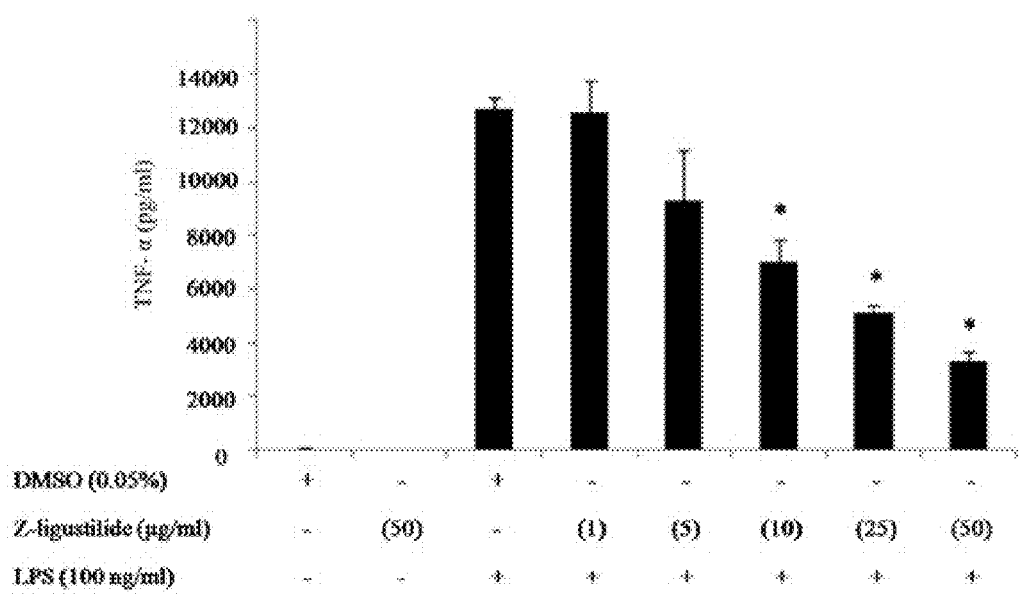
FIG. 8 shows the dose-dependent effect of Z-ligustilide on TNF-α protein production in BV-2 cells. ($p<0.05$, compared with DMSO+LPS only).

The results, as shown in FIGS. 7 and 8, reveal that the application of Sen A and Z-Lig at a concentration of 5 and 10 µg/ml, respectively, significantly inhibits TNF-α production. Specifically, senkyunolide A at a concentration of 10 µg/ml, 25 µg/ml, and 50 µg/ml produces an approximately 2-fold, 4-fold, and 10-fold reduction in TNF-α production, respectively. Z-ligustilide also inhibits TNF-α production in a dose-dependent manner (FIG. 8).

Example 6

Molecular Mechanisms of Downregulation of TNF-α Production

The molecular pathways involved in senkyunolide A inhibition of TNF-α production are elucidated. It is well documented that the activation of cytokine production in LPS-treated cells is initiated by the binding of LPS to its receptor[29]. After binding to the receptor, a cascade of signaling kinases is activated. Among the activated kinases, MAP kinases play a crucial role in LPS-induced cytokine production. Previous studies illustrated that the induction of TNF-α by LPS and other pathogens requires the phosphorylation and activation of ERK1/2 and p38 MAPK[30].

Figure 9A:
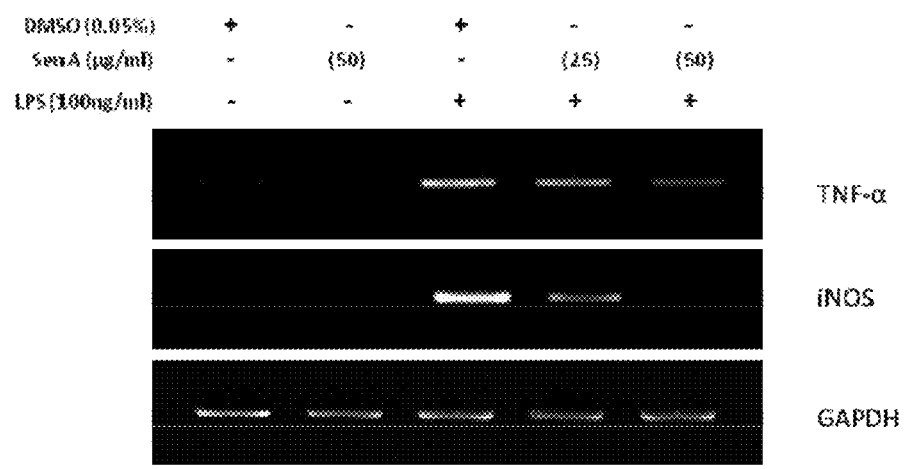
FIGS. 9A-C show the effect of senkyunolide A on TNF-α mRNA expression and iNOS expression in BV-2 cells.
Figure 9B:
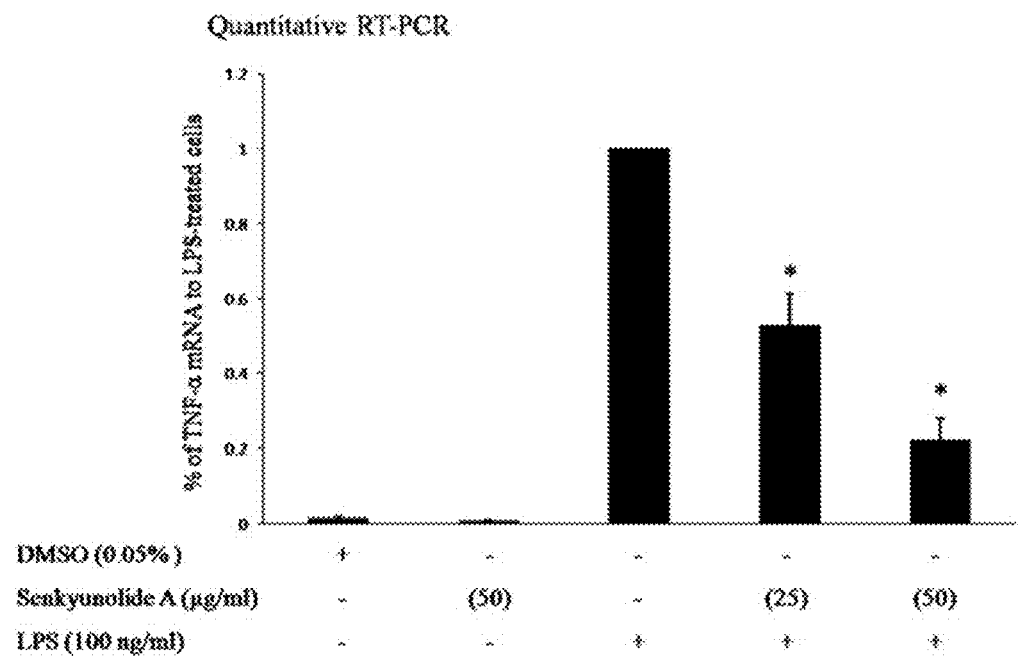
Figure 9C:
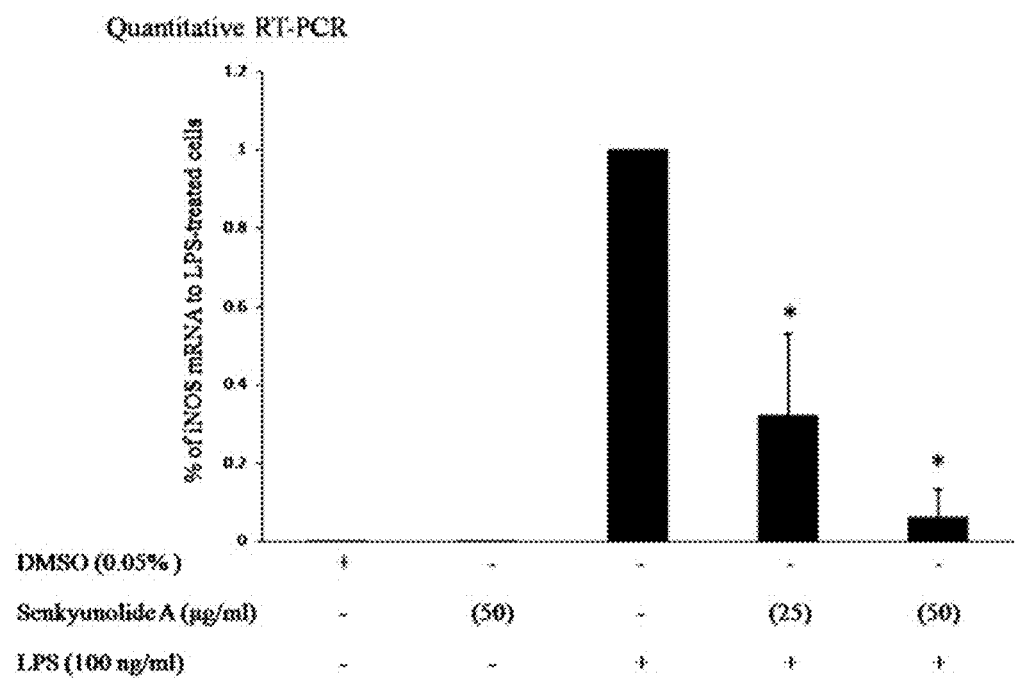

To study the role of senkyunolide A in suppressing TNF-α production, $10^5$ cells/ml BV-2 cells are seeded in 24-well plates (0.5 ml in each well). Cells are treated with senkyunolide A at various concentrations for 1 hour prior to the addition of LPS for another 6 hours. Total RNA of the treated samples is isolated and subjected to semi-quantitative RT-PCR assays (FIG. 9A) and quantitative RT-PCR assays (FIGS. 9B and C) using specific human TNF-α primers. The results, as shown in FIG. 9, reveal that senkyunolide A inhibits TNF-α mRNA and iNOS expression.

Figure 10:
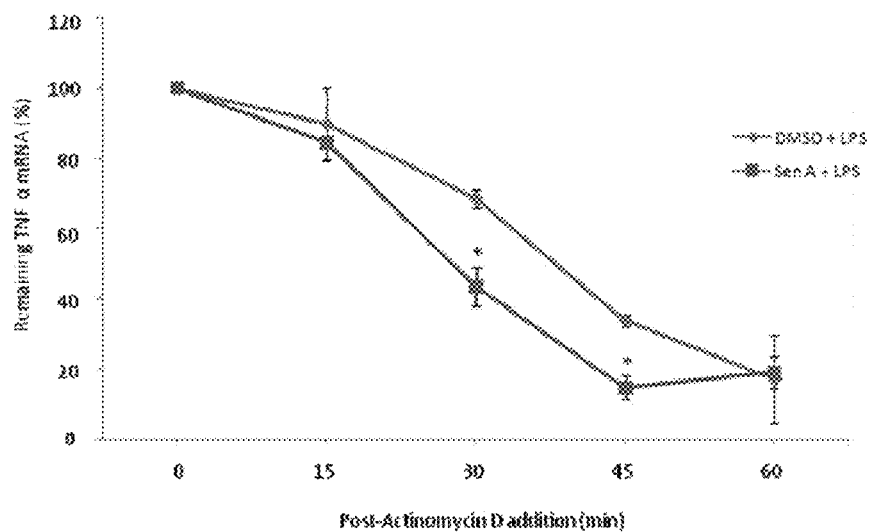
FIG. 10 shows the effect of senkyunolide A on TNF-α mRNA stability in BV-2 cells. (p<0.05, compared with DMSO+LPS only).

In addition, the effect of senkyunolide A on TNF-α mRNA stability is evaluated. Specifically, $10^5$ cells/ml BV-2 cells are seeded in 24-well plates (0.5 ml in each well). Cells are treated with Sen A at various concentrations for 1 hour prior to the addition of LPS for another 2 hours, and further incubated with 1 µg/ml actinomycin for various time periods. Total RNA of the treated samples is isolated and subjected to real-time RT-PCR. The results, as shown in FIG. 10, reveal that senkyunolide A destabilizes TNF-α mRNA. In the presence of senkyunolide A, there was a significant increase in the degradation of TNF-α mRNA, whose half life was reduced by 43%.

Figure 12A:
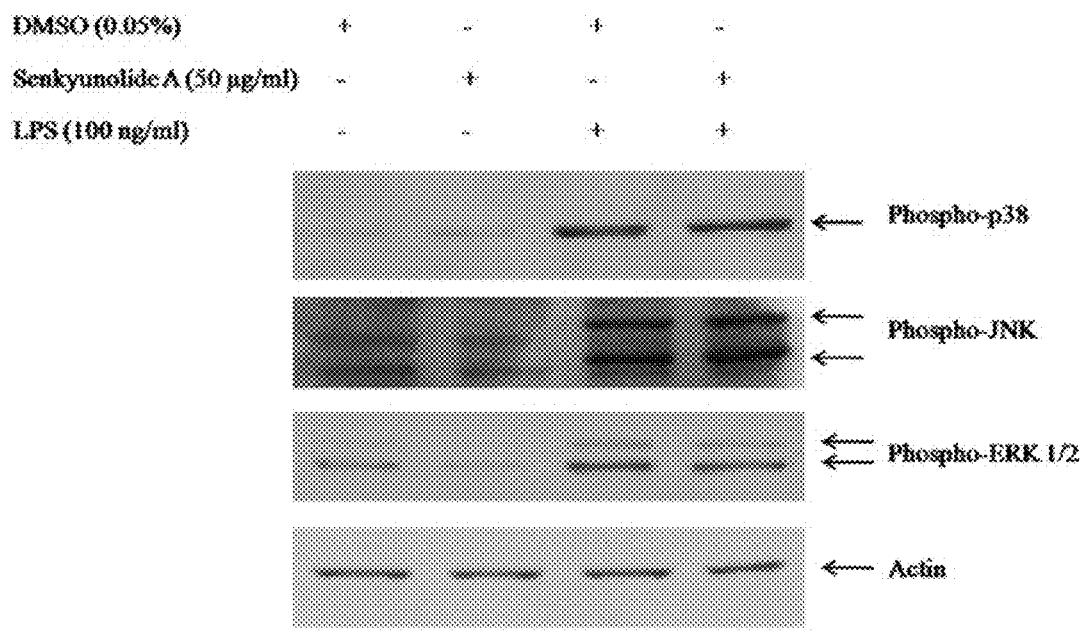
FIGS. 12A-B show that senkyunolide A does not affect the phosphorylation of MAPKs and the nuclear translocation of NF-kB in LPS-stimulated BV-2 cells. BV-2 cells ($2 \times 10^5$ cells/ml) were pretreated with either 0.05% DMSO or 50 μg/ml senkyunolide A for 1 h, followed by treatment with 100 ng/ml LPS for another 30 min. (A) Cytoplasmic proteins were extracted and analyzed by Western Blot using antibodies specific for phospho-p38, phospho-JNK, phospho-ERK 1/2 and actin. (B) Nuclear proteins were extracted and analyzed by Western Blot against NF-kB p65 and lamin B antibodies.

Further, it is discovered that Sen A does not affect the phosphorylation of MAPKs and the nuclear translocation of NF-kB in LPS-stimulated BV-2 cells. Briefly, the effect of Sen A on mitogen-activated protein kinases (MAPKs) in the cell signaling cascade was investigated. The effects of senkyunolide A on the phosphorylation of MAP kinases, including p38, JNK and ERK ½, were examined in LPS-stimulated BV-2 cells. FIG. 12A shows that LPS increased the levels of phosphorylation of all three MAPKs. Pretreatment with senkyunolide A did not exert any effect on the levels of phosphorylation of MAPKs.

Figure 12B:
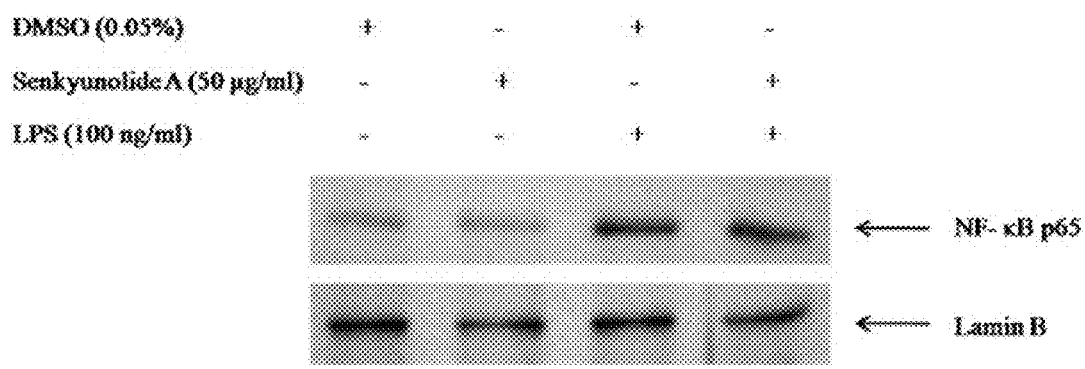

The NF-kB pathway plays a key role in the transcriptional regulation of inflammatory mediators. The effects of senkyunolide A on NF-kB translocation into the nucleus in LPS-induced BV-2 cells were also studied. As shown FIG. 12B, pretreatment with senkyunolide A did not exert an inhibitory effect on the translocation of NF-kB p65 into the nucleus of BV-2 cells activated by LPS. The results indicate that the inhibitory effect of senkyunolide A on TNF-α and iNOS induction is independent of MAPK and NF-kB signaling pathways.

Example 7

Cytoprotective Effect of Senkyunolide A and Z-Ligustilide

This Example shows that senkyunolide A (Sen A) and Z-ligustilide (Z-Lig), via the inhibition of pro-inflammatory mediators, reduce cytotoxicity during neuroinflammation and protect neuronal cells from cell death.

Z-ligustilide (Z-Lig) suppresses cell death caused by hydrogen peroxide-induced cell injury. Briefly, PC-12 cells ($5 \times 10^4$ cells/ml) are seeded in 24-well culture plates (0.5 ml in each well). The cells are treated with Z-ligustilide, followed by treatment with hydrogen peroxide to induce cell injury. The treated cells are incubated with 0.5 mg/ml MTT solution (Sigma Aldrich, St. Louis, Mo.) for 1 h at 37° C. The medium is discarded and 200 μl isopropyl alcohol (IPP) is then added. After 15 min of incubation, the absorbance is measured at 570 nm.

Figure 11:
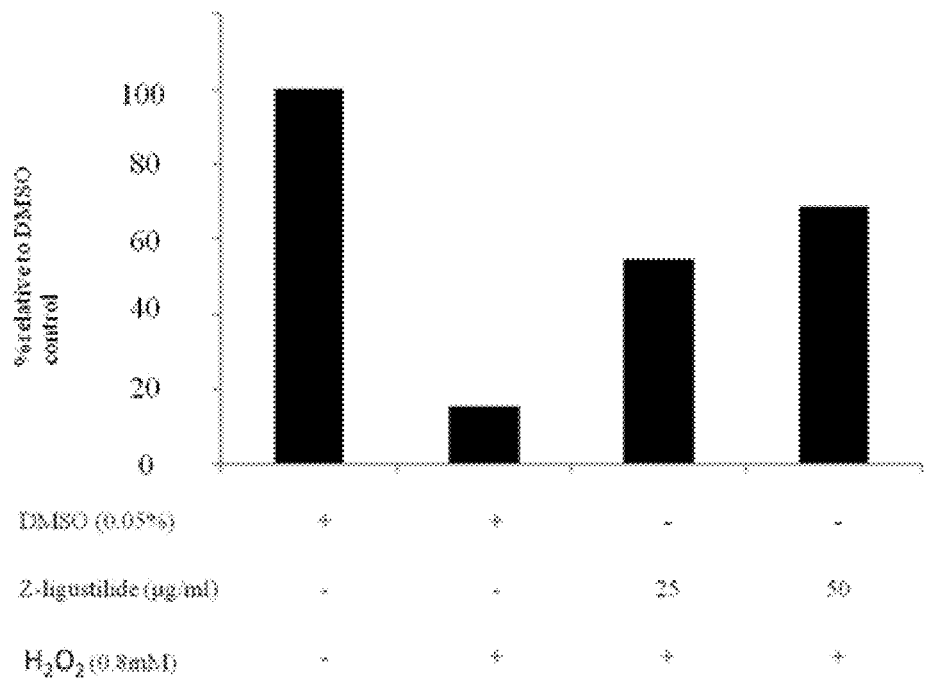
FIG. 11 shows the effect of Z-ligustilide on hydrogen peroxide-induced death of PC-12 cells. PC-12 cells were pretreated with either DMSO (0.05%) or Z-ligustilide for 24 h, followed by treatment with 0.8 mM $H_2O_2$ for another 6 h. Cell viability was measured using MTT assays. A set of representative results is shown.

The results, as shown in FIG. 11, reveal that hydrogen peroxide causes a marked decrease in cell viability. Treatment with 25 μg/ml Z-Lig increases cell viability from 17% to 57%. Treatment with 50 μg/ml Z-Lig further increases cell viability to 70%. The results reveal that Z-Lig protects cells from hydrogen peroxide-induced cell death.

Figure 13:
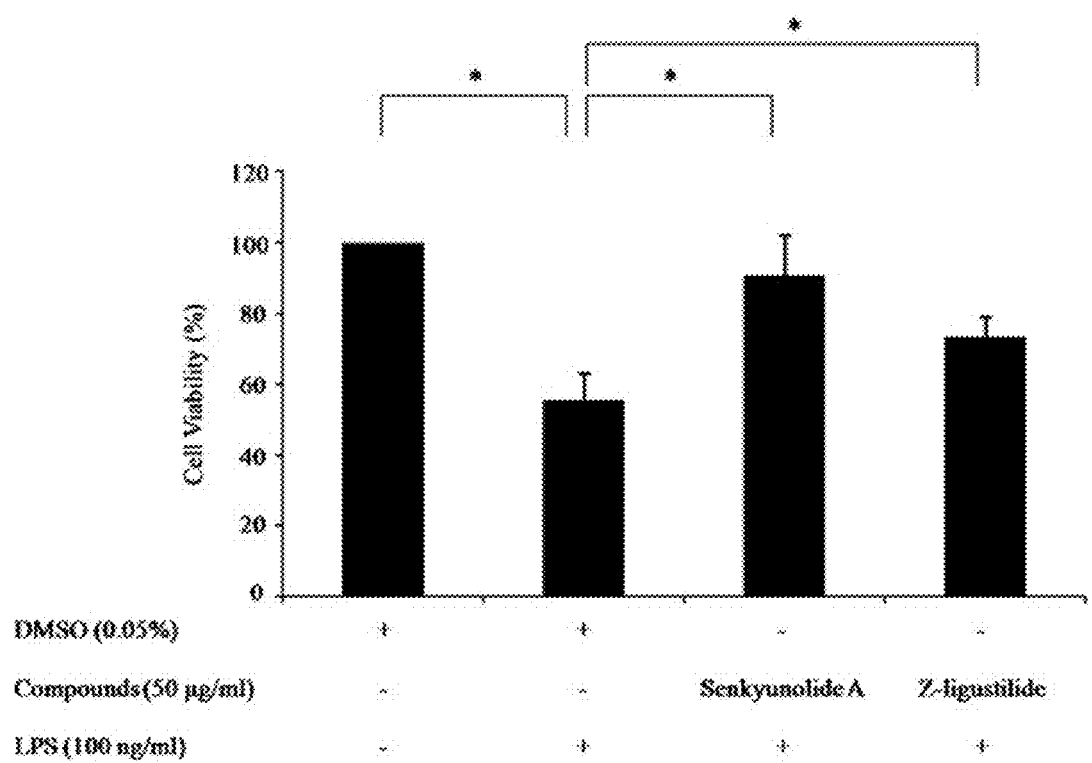
FIG. 13 shows that senkyunolide A and Z-ligustilide protect Neuro-2a from cell death induced by conditioned medium from LPS-treated BV-2 cells. BV-2 cells ($3 \times 10^5$ cells/ml) were first treated with 100 ng/ml LPS for 18 h, in the presence of either 0.05% DMSO or 50 μg/ml senkyunolide A or Z-ligustilide. After centrifugation, the supernatants from BV-2 cells were transferred to Neuro-2a cells ($5 \times 10^4$ cells/ml) for 48 h. Viability of Neuro-2a cells was measured using MTT assays. Results are shown as mean SD from three independent experiments. *p<0.05 compared with DMSO+LPS.

FIG. 13 shows that both senkyunolide A and Z-ligustilide inhibit the production of TNF-α and nitrite in microglial cells challenged with LPS. Briefly, to investigate the physiological significance of Sen A and Z-Lig, a conditioned culture medium transfer model, commonly used for studying neuronal cell death induced by microglial activation, was adopted. After BV-2 cells were challenged with LPS, the supernatants were collected and centrifuged. The conditioned culture media were then transferred to Neuro-2a cell cultures. After 48 h incubation, more than 40% of Neuro-2a cells exhibited cell death (FIG. 13). This shows that the conditioned culture medium produced from LPS-activated BV-2 cells causes cell death in Neuro-2a cells.

Advantageously, supernatants of BV-2 cells treated with either senkyunolide A or Z-ligustilide, exhibited reduced toxicity to neuroblast cells. Specifically, a significant reduction in cell death, to less than 15% and 25%, respectively, was observed. Neuro-2a cells, treated with LPS, senkyunolide A, or Z-ligustilide alone in the culture media, did not show cell death (data not shown).

All references, including publications, patent applications and patents, cited herein are hereby incorporated by reference to the same extent as if each reference was individually and specifically indicated to be incorporated by reference and was set forth in its entirety herein.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the examples and embodiments described herein are for illustrative purposes only and that various modifications or changes in light thereof will be suggested to persons skilled in the art and are to be included within the spirit and purview of this application.

REFERENCES

[1] Ohlsson K, Bjork P, Bergenfeldt M, Hageman R, Thompson R C. Interleukin-1 receptor antagonist reduces mortality from endotoxin shock. Nature. 1990; 348:550-552.

[2] Tracey K J, Fong Y, Hesse D G, et al. Anti-cachectin/TNF monoclonal antibodies prevent septic shock during lethal bacteraemia. Nature. 1987; 330:662-664.

[3] Montesano R, Soulie P, Eble J A, Carrozzino F. Tumour necrosis factor alpha confers an invasive, transformed phenotype on mammary epithelial cells. J Cell Sci. 2005; 118:3487-3500.

[4] Raetz C R. Biochemistry of endotoxins. Annu Rev Biochem. 1990; 59:129-170.

[5] Bone R C. Gram-negative sepsis. Background, clinical features, and intervention. Chest. 1991; 100:802-808.

[6] Raetz C R, Ulevitch R J, Wright S D, Sibley C H, Ding A, Nathan C F. Gram-negative endotoxin: an extraordinary lipid with profound effects on eukaryotic signal transduction. Faseb J. 1991; 5:2652-2660.

[7] Tracey K J, Cerami A. Tumor necrosis factor: a pleiotropic cytokine and therapeutic target. Annu Rev Med. 1994; 45:491-503.

[8] Aggarwal B B, Shishodia S. Sandur S K, Pandey M K, Sethi G. Inflammation and cancer: how hot is the link? Biochem Pharmacol. 2006; 72:1605-1621.

9 Woodworth C D, McMullin E, Iglesias M, Plowman G D. Interleukin 1 alpha and tumor necrosis factor alpha stimulate autocrine amphiregulin expression and proliferation of human papillomavirus-immortalized and carcinoma-derived cervical epithelial cells. Proc Natl Acad Sci USA. 1995; 92:2840-2844.

10 Montesano R, Soulie P, Eble J A, Carrozzino F. Tumour necrosis factor alpha confers an invasive, transformed phenotype on mammary epithelial cells. J Cell Sci. 2005; 118:3487-3500.

11 Raetz C R. Biochemistry of endotoxins. Annu Rev Biochem. 1990; 59:129-170.

12 Cheng S M, Xing B, Li J C, Cheung B K, Lau A S, Interferon-gamma regulation of TNF alpha-induced matrix metalloproteinase 3 expression and migration of human glioma T98G cells. Int J Cancer. 2007 Sep. 15; 121(6):1190-6

13 Law A H, Lee D C, Cheung B K, Yim H C, Lau A S., J Virol. Role for nonstructural protein 1 of severe acute respiratory syndrome coronavirus in chemokine dysregulation. 2007 January; 81(1):416-22. Epub 2006 Oct. 11.

14 Cheung B K, Lee D C, Li J C, Lau Y L, Lau A S., A role for double-stranded RNA-activated protein kinase PKR in *Mycobacterium*-induced cytokine expression. J. Immunol. 2005 Dec. 1; 175(10:7218-25.

15 Lee D C, Cheung C Y, Law A H, Mok C K, Peiris M, Lau A S., p38 mitogen-activated protein kinase-dependent hyperinduction of tumor necrosis factor alpha expression in response to avian influenza virus H5N1.

16 Li J C, Lee D C, Cheung B K, Lau A S., Mechanisms for HIV Tat upregulation of IL-10 and other cytokine expression: kinase signaling and PKR-mediated immune response. FEBS Lett. 2005 Jun. 6; 579(14):3055-62.

17 Yim H C, Li J C, Lau J S, Lau A S., HIV-1 Tat dysregulation of lipopolysaccharide-induced cytokine responses: microbial interactions in HIV infection. AIDS. 2009 Jul. 31; 23(12):1473-84.

18 Cheng S M, Li J C, Lin S S, Lee D C, Liu L, Chen Z, Lau A S., HIV-1 transactivator protein induction of suppressor of cytokine signaling-2 contributes to dysregulation of IFN {gamma} signaling. Blood. 2009 May 21; 113(21): 5192-201. Epub 2009 Mar. 11.

19 Barone F C, Feuerstein G Z. Inflammatory mediators and stroke: New opportunities for novel therapeutics. Journal of Cerebral Blood Flow and Metabolism 1999; 19: 819-834.

20 Chamorro A, Hallenbeck J. The harms and benefits of inflammatory and immune responses in vascular disease. Stroke 2006; 37:291-293.

21 Samson Y, Lapergue B, Hosseini H. Inflammation and ischaemic stroke: current status and future perspectives. Revue Neurologique 2005; 161:1177-1182.

22 Shohami E, Ginis I, Hallenbeck J M. Dual role of tumor necrosis factor alpha in brain injury. Cytokine & Growth Factor Reviews 1999; 10:119-130.

23 Irving E A, Bamford M. Role of mitogen- and stress-activated kinases in ischemic injury. Journal of Cerebral Blood Flow and Metabolism 2002; 22:631-647.

24 Wang Q, Tang X N, Yenari M A. The inflammatory response in stroke. Journal of Neuroimmunology 2007; 184:53-68.

25 Blasi F, Barluzzi R, Bocchini V, Mazzolla R, Bistoni F. Immortalization of Murine Microglial Cells by a V-Raf/V-Myc Carrying Retrovirus. Journal of Neuroimmunology 1990; 27:229-237.

26 Schmitz G, Leuthäauser-Jaschinski K, Orsó E. Are circulating monocytes as microglia orthologues appropriate biomarker targets for neuronal diseases? Central Nervous Systems Agents in Medicinal Chemistry 2009; 9:307-330.

27 Yang C L H. Chik S C C, Li J C B., Cheung B K W, Lau A S Y. Identification of the Bioactive Constituent and Its Mechanisms of Action in Mediating the Anti-inflammatory Effects of Black Cohosh and Related *Cimicifuga* species on Human Primary Blood Macrophages. Journal of Medicinal Chemistry 2009; 52:6707-6715.

28 Lee D C W, Cheung C Y, Law A H Y, Mok C K P, Peiris M, Lau A S Y. p38 mitogen-activated protein kinase-dependent hyperinduction of tumor necrosis factor alpha expression in response to avian influenza virus H5N1. Journal of Virology 2005; 79:10147-10154.

29 Lu Y C, Yeh W C, Ohashi P S. LPS/TLR4 signal transduction pathway. Cytokine. 2008; 42:145-151.

30 Kim S H, Kim J, Sharma R P. Inhibition of p38 and ERK MAP kinases blocks endotoxin-induced nitric oxide production and differentially modulates cytokine expression. Pharmacol Res. 2004; 49:433-439.

31

We claim:

1. A method for treating stroke, wherein said method comprises: administering, to a subject in need of such treatment, an effective amount of an isolated compound that is senkyunolide A or a salt thereof, wherein senkyunolide A has the following formula:

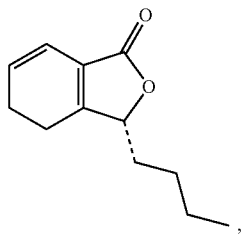

and determining the presence and/or level of nitric oxide in the subject, wherein the determination is made at multiple times to monitor changes in the presence and/or level over time, and wherein the effective amount of senkyunolide A is at or above 10 µg/mL and the administration of said senkyunolide A causes a reduction in nitric oxide production in the subject.

2. The method, according to claim 1, wherein the subject is a human.

* * * * *

UNITED STATES PATENT AND TRADEMARK OFFICE
CERTIFICATE OF CORRECTION

PATENT NO. : 9,655,877 B2
APPLICATION NO. : 13/005301
DATED : May 23, 2017
INVENTOR(S) : Allan Sik Yin Lau et al.

It is certified that error appears in the above-identified patent and that said Letters Patent is hereby corrected as shown below:

In the Specification

Column 15,
Line 15, "(lipopolysachamide, LYS)" should read --(lipopolysacharride, LPS)--.

Column 21,
Line 1, "including p38, INK and ERK ½," should read --including p38, JNK and ERK ½.--.

Column 23,
Line 26, "2005 Dec. 1; 175(10:7218-25." should read --2005 Dec 1; 175(11):7218-25.--.

Signed and Sealed this
Twentieth Day of February, 2018

Andrei Iancu
*Director of the United States Patent and Trademark Office*